(12) United States Patent
Murayama et al.

(10) Patent No.: US 7,722,551 B2
(45) Date of Patent: May 25, 2010

(54) GUIDE WIRE

(75) Inventors: Hiraku Murayama, Shizuoka (JP); Akihiko Umeno, Shizuoka (JP); Jun Iwami, Shizuoka (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 163 days.

(21) Appl. No.: 10/635,665

(22) Filed: Aug. 7, 2003

(65) Prior Publication Data

US 2004/0030265 A1 Feb. 12, 2004

(30) Foreign Application Priority Data

Aug. 9, 2002 (JP) ............... 2002-233905
Aug. 9, 2002 (JP) ............... 2002-233906

(51) Int. Cl.
*A61M 25/00* (2006.01)
*A61M 5/178* (2006.01)

(52) U.S. Cl. .................... 600/585; 604/164.13

(58) Field of Classification Search ......... 600/585; 604/164.13

See application file for complete search history.

(56) References Cited

U.S. PATENT DOCUMENTS

| 4,925,445 | A | | 5/1990 | Sakamoto et al. |
| 5,213,111 | A | | 5/1993 | Cook et al. |
| 5,341,818 | A | * | 8/1994 | Abrams et al. ............. 600/585 |
| 5,358,796 | A | | 10/1994 | Nakamura et al. |
| 5,365,943 | A | * | 11/1994 | Jansen ...................... 600/585 |
| 5,368,661 | A | | 11/1994 | Nakamura et al. |
| 5,411,476 | A | | 5/1995 | Abrams et al. |
| 5,769,796 | A | * | 6/1998 | Palermo et al. ............. 600/585 |
| 6,001,068 | A | * | 12/1999 | Uchino et al. .............. 600/585 |
| 6,142,975 | A | | 11/2000 | Jalisi et al. |
| 6,248,082 | B1 | | 6/2001 | Jafari |
| 6,488,637 | B1 | | 12/2002 | Eder et al. |
| 6,702,762 | B2 | * | 3/2004 | Jafari et al. ................ 600/585 |
| 7,074,197 | B2 | * | 7/2006 | Reynolds et al. ........... 600/585 |
| 2002/0049392 | A1 | | 4/2002 | DeMello |

FOREIGN PATENT DOCUMENTS

| DE | 196 07 595 A1 | 9/1997 |
| EP | 0 838 230 A2 | 4/1998 |
| EP | 0 917 885 A1 | 5/1999 |
| JP | 1-124473 | 5/1989 |
| WO | WO 01/36034 A2 | 5/2001 |
| WO | WO 03/057273 A2 | 7/2003 |

* cited by examiner

*Primary Examiner*—Max Hindenburg
*Assistant Examiner*—Jeffrey G Hoekstra
(74) *Attorney, Agent, or Firm*—Buchanan Ingersoll & Rooney PC

(57) ABSTRACT

A guide wire includes a wire body and a coil provided so as to cover the distal side of the wire body. The wire body has a first wire disposed on the distal side, a second wire disposed on the proximal side from the first wire, and a third wire disposed on the proximal side from the second wire. The first wire is made from a reshapable metal material such as a stainless steel. The second wire is made from a pseudo-elastic alloy such as a Ni-Ti alloy. The third wire is made from a material having an elastic modulus larger than that of a material for forming the second wire. The first wire and the second wire are joined to each other by welding, and similarly the second wire and the third wire are joined to each other by welding.

33 Claims, 12 Drawing Sheets

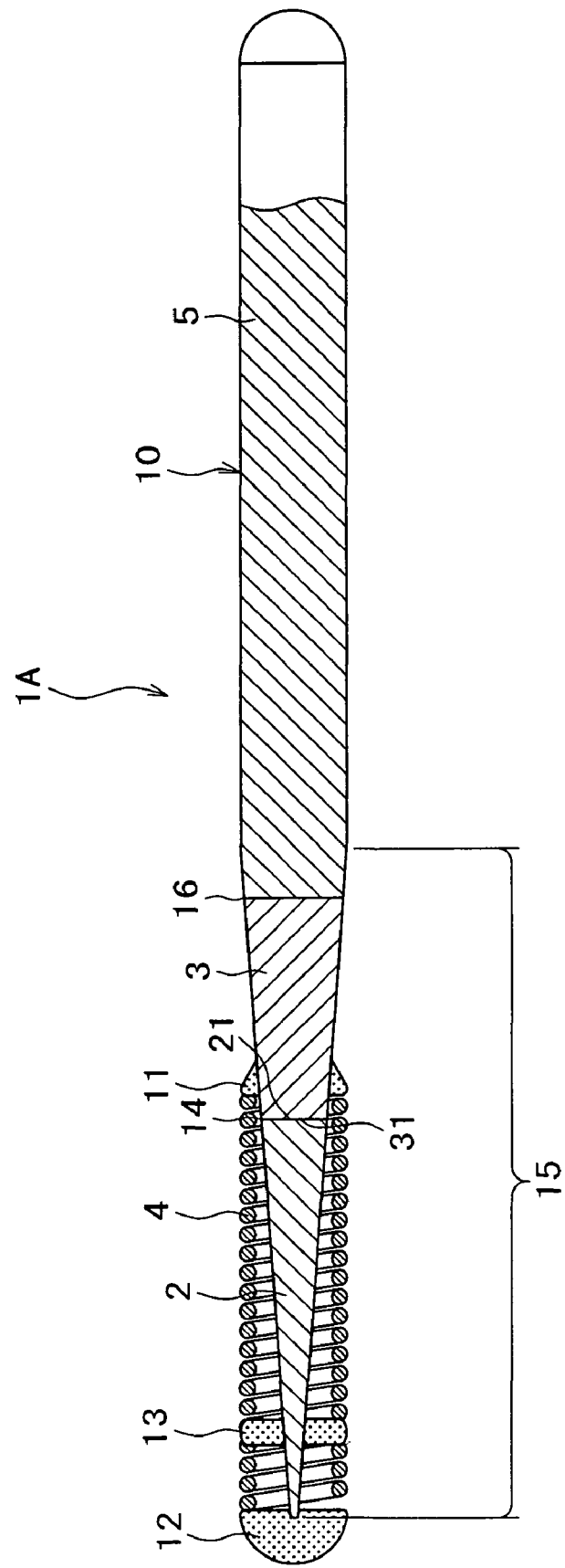

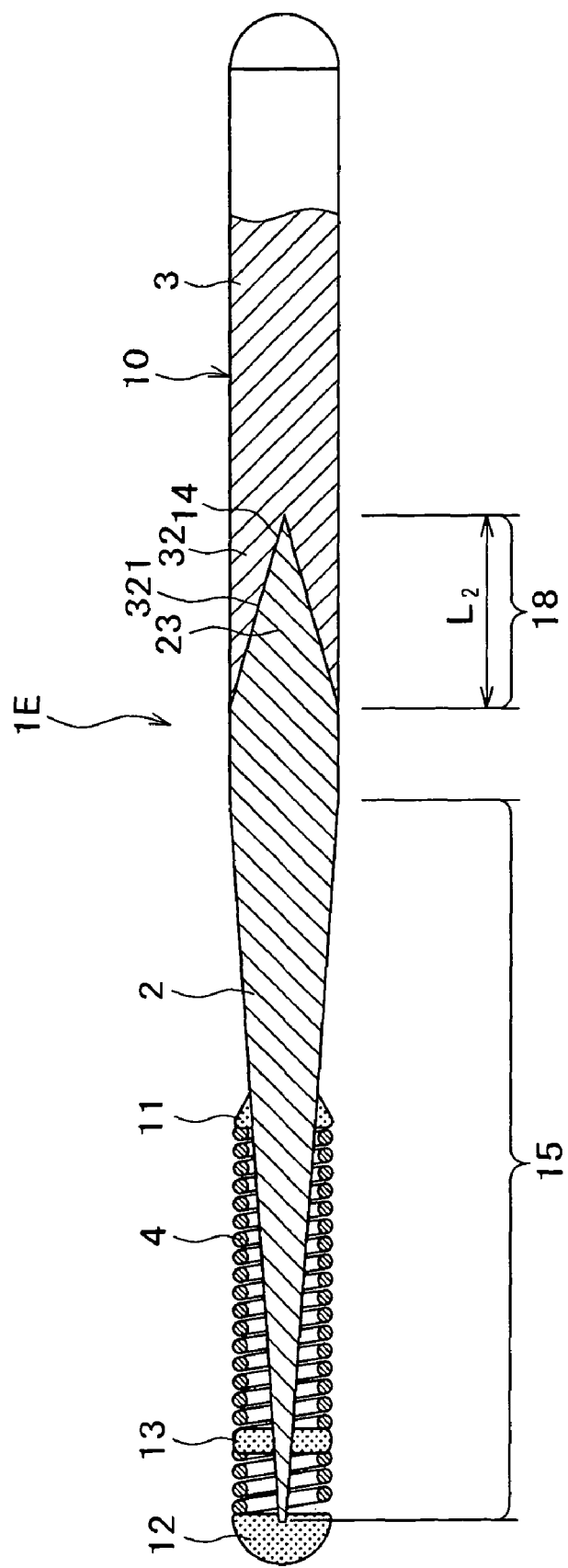

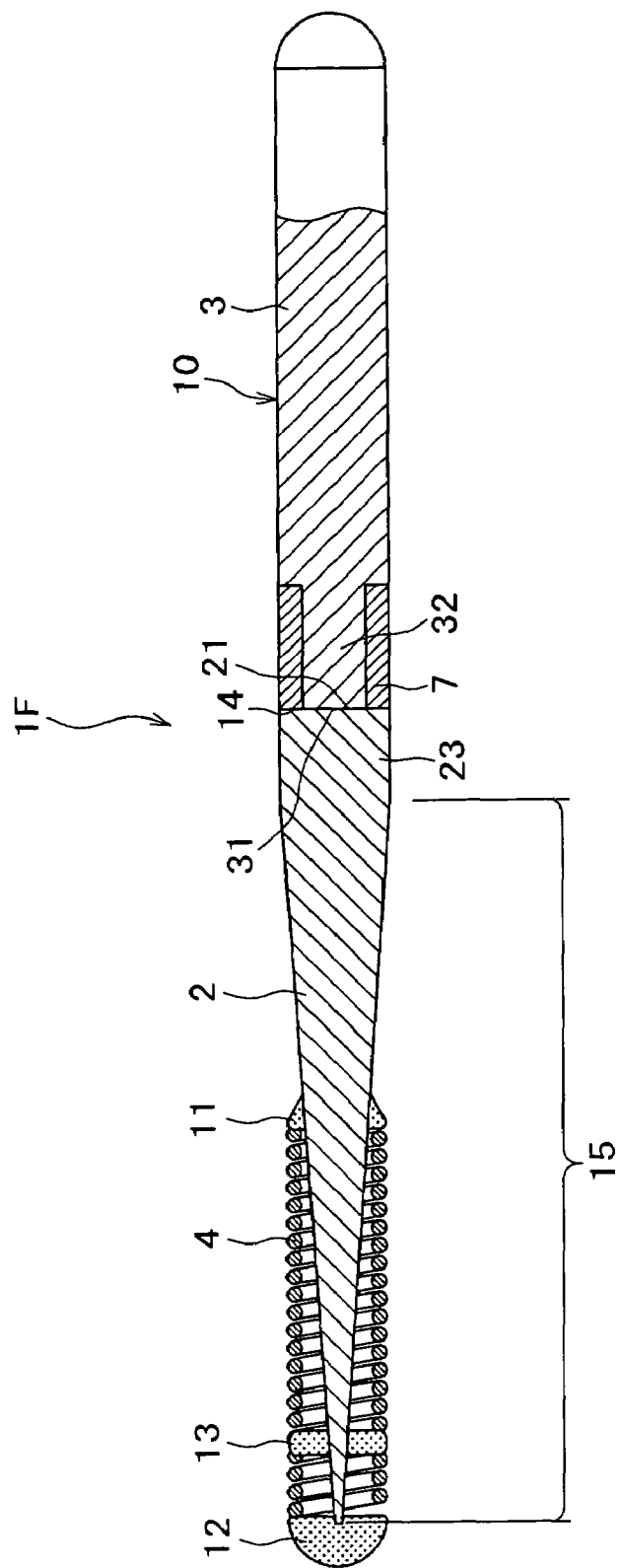

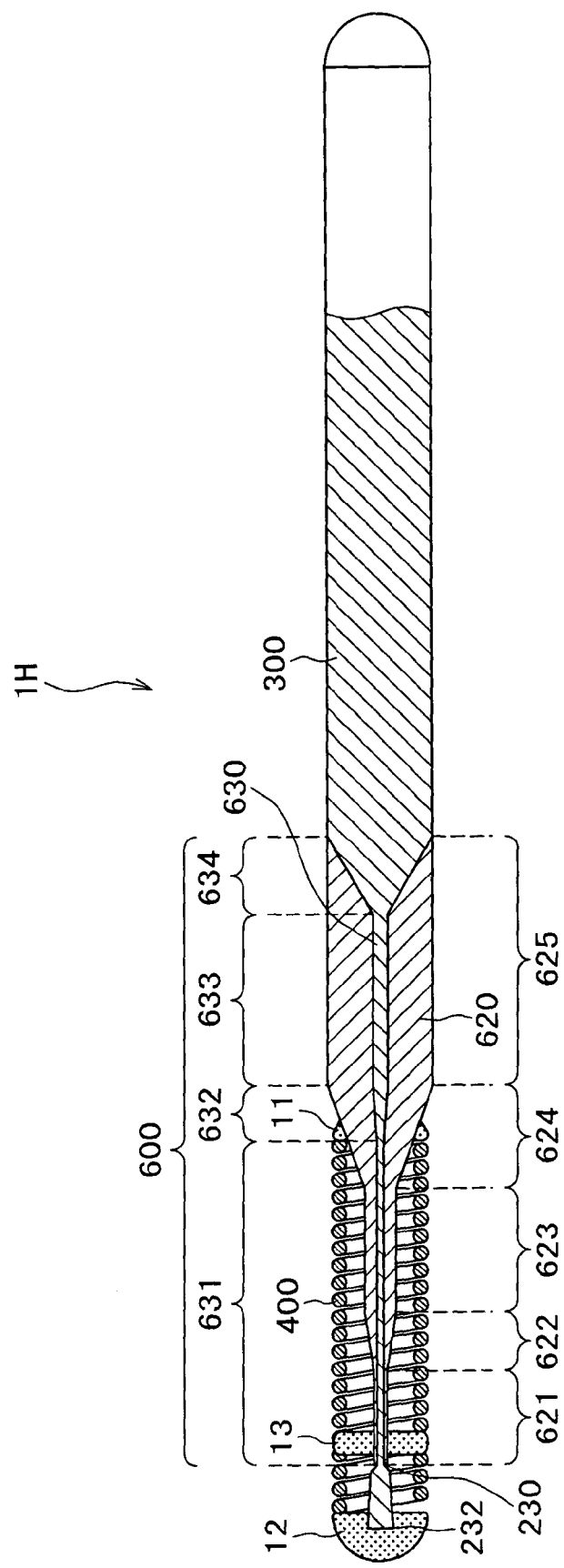

GUIDE WIRE

BACKGROUND OF THE INVENTION

The present invention relates to a guide wire, particularly to a guide wire used to guide a catheter in a body lumen such as a blood vessel.

Guide wires are used to guide a catheter in treatment of cites at which open surgeries are difficult or which require minimal invasiveness to the body such as PTCA (Percutaneous Transluminal Coronary Angioplasty), or in examination such as cardio-angiography. A guide wire used in the PTCA is inserted, with the distal end projecting from the distal end of a balloon catheter, into the vicinity of a target angiostenosis portion together with the balloon catheter, and is operated to guide the distal end portion of the balloon catheter to the target angiostenosis portion.

A guide wire used to insert a balloon catheter into a blood vessel complicatedly bent requires appropriate flexibility, pushability and torque transmission performance (generically called "operationality") for transmitting an operational force from the proximal end portion to the distal side, and kink resistance (resistance against sharp bending). To meet such requirements, superelastic materials such as a Ni—Ti alloy for improving the flexibility and restoring performance have been desirably used as materials for forming a core member (wire body) of a guide wire.

To select one of branched blood vessels, a distal end portion of a guide wire is often bent into a desired shape by an operator. The operation of bending a distal end portion of a guide wire into a desired shape is called "reshaping".

In the case of using a wire body made from a superelastic alloy such as a Ni—Ti alloy, however, it is difficult to reshape such a wire body because the wire body has super-elasticity. Accordingly, a reshaping ribbon made from a reshapable material, for example, a stainless steel is required to be additionally provided on the wire body. In this case, since the Ni—Ti alloy used as the material for forming the wire body is poor in wettability against solder, the joining strength of the solder becomes poor, and to enhance the joining strength of the solder, it is required to perform a special treatment of removing an oxide layer on the surface of the Ni—Ti alloy and preliminarily covering the metal surface with tin in a state that the metal is blocked from contacting with air. As a result, it takes a lot of labor and time to produce the wire body made from a Ni—Ti alloy provided with a reshapable ribbon made from a stainless steel.

Conventional guide wires include a core member that is substantially made from a single material. In particular, to enhance the operationality of the guide wire, a material having a relatively high elastic modulus is used as the material of the core member. The guide wire including such a core member, however, has an inconvenience that the distal end portion of the guide wire becomes low in flexibility. On the other hand, if a material having a relatively low elastic modulus is used as the material of the core member for increasing the flexibility of the distal end portion of the guide wire, the operationality of the proximal end portion of the guide wire is degraded. In this way, it has been regarded as difficult to satisfy both requirements associated with the flexibility and operationality by using a core member made from a single material.

SUMMARY OF THE INVENTION

An object of the present invention is to provide a guide wire excellent in operationality. Another object of the present invention is to provide a guide wire capable of enhancing the operationality with a simple structure and easily, certainly reshaping a distal end portion of the guide wire. A further object of the present invention is to provide a guide wire excellent in operationality and in kink resistance.

To achieve the above object, according to a first aspect of the present invention, there is provided a guide wire including a first wire disposed on the distal side of the guide wire, the first wire being made from a reshapable material, and a second wire disposed on the proximal side from the first wire, the second wire being made from a pseudo-elastic alloy, wherein the first wire and the second wire are joined to each other by welding.

The guide wire preferably includes a third wire disposed on the proximal side from the second wire, the third wire being made from a material having an elastic modulus larger than an elastic modulus of the material for forming the second wire, wherein the second wire and second third wire are joined to each other by welding.

Each of outer diameters of the first wire and the second wire may be gradually reduced in the direction toward the distal end in a region extending across the welded portion from a position on the proximal side from a welded portion between the first wire and the second wire to a position on the distal side from the welded portion.

The first wire may have a small cross-sectional area portion having a cross-sectional area smaller than a cross-sectional area of a distal end portion of the second wire, the small cross-sectional area portion being disposed in the vicinity of a welded portion between the first wire and the second wire.

The guide wire may further includes an overlapping portion in which a proximal end portion of the first wire and a distal end portion of the second wire are overlapped to each other in the axial direction of the first and second wires, wherein the first wire and second wire are welded to each other in the overlapping portion.

The guide wire may further includes a rigidity imparting member for increasing a rigidity of the vicinity of a distal end portion of the second wire, the rigidity imparting member being disposed in the vicinity of the proximal side of a welded portion between the first wire and the second wire in such a manner as to cover the outer periphery of the second wire.

The second wire may be made from a stainless steel.

Each of a connection end face of the first wire to the second wire and a connection end face of the second wire to the first wire may be nearly perpendicular to the axial direction of both the wires.

The guide wire may further include a spiral coil provided so as to cover at least a distal end portion of the first wire.

The welded portion between the first wire and the second wire may be located on the proximal side from the proximal end of the coil.

The welded portion between the first wire and the second wire may be located on the distal side from the proximal end of the coil.

The guide wire may be used in such a manner that the welded portion between the first wire and the second wire be located in a living body.

The third wire may be made from a stainless steel or a cobalt alloy.

The welding may be performed by a butt resistance welding process.

The flexural rigidity of the distal end of the second wire may be nearly equal to that of proximal end of the first wire.

The guide wire may further include a step filling member for filling a stepped portion formed on the outer periphery of the welded portion.

The overlapping portion may have a portion in which the occupied ratio of the cross-sectional area of the second wire to the cross-sectional area of the overlapping portion is gradually reduced in the direction toward the distal end.

The proximal end portion of the first wire may be formed into a conical or truncated conical shape with its outer diameter gradually reduced in the direction toward the proximal end, the distal end portion of the second wire be formed into a shape having a conical or truncated conical hollow portion with its outer diameter gradually reduced in the direction toward the proximal end, wherein the first wire and the second wire be welded to each other in a state that the proximal end portion of the first wire be inserted in the hollow portion of the second wire.

The distal end portion of the second wire may be formed into a conical or truncated conical shape with its outer diameter gradually reduced in the direction toward the distal end, the proximal end portion of the first wire be formed into a shape having a conical or truncated conical hollow portion with its outer diameter gradually reduced in the direction toward the distal end, wherein the first wire and the second wire be welded to each other in a state that the distal end portion of the second wire be inserted in the hollow portion of the first wire.

The rigidity imparting member may be made from a material having an elastic modulus larger than that of the material for forming the second wire.

The rigidity imparting member may be formed into a tubular shape or a coil shape.

The guide wire may further include a cover layer made from a resin material, wherein the cover layer be provided so as to cover the outer peripheries of at least parts of the first wire and the second wire.

To achieve the above object, according to a second aspect of the present invention, there is provided a guide wire including a distal side wire disposed on the distal side of the guide wire, the distal side wire being made from a reshapable metal material, an intermediate wire disposed on the proximal side from the distal side wire, at least an outer layer of the intermediate wire being made from a pseudo-elastic alloy, and a proximal side wire disposed on the proximal side from the intermediate wire, the proximal side wire being made from a material having an elastic modulus larger than an elastic modulus of the pseudo-elastic alloy.

The intermediate wire and the proximal side wire are preferably joined to each other by welding.

To achieve the above object, according to a third aspect of the present invention, there is provided a guide wire including a first wire including a tubular wire disposed on the distal side of the guide wire and a core member provided so as to pass through the tubular wire, the core member being made from a material having an elastic modulus larger than an elastic modulus of a material for forming the tubular wire, and a second wire integrally connected to the proximal side of the first wire, the second wire being made from a material having an elastic modulus larger than the elastic modulus of the material for forming the tubular wire.

The core member of the first wire is preferably exposed at a distal end portion of the first wire.

The exposed length of the core member at the distal end portion of the first wire may be in a range of 5 to 200 mm.

The guide wire may further include a spiral coil provided so as to cover at least a portion, from which the core member is exposed, of the first wire.

The tubular wire may have, at least on the distal side, an outer diameter gradually reduced in the direction toward the distal end.

Preferably, letting a maximum outer diameter of the tubular wire be $R_1$ (mm) and an average outer diameter of the core member be $R_2$ (mm), a ratio of $R_2/R_1$ is in a range of 0.01 to 0.5.

The joining portion between the first wire and the second wire may be located on the proximal side from the proximal side of the coil.

At least the tubular wire of the first wire and the second wire may be welded to each other.

The welding may be performed by a butt resistance welding process.

The elastic modulus of the material for forming the core member may be nearly equal to that of the material for forming the second wire.

Each of the core member and the second wire may be made from a stainless steel.

The tubular wire may be made from a superelastic alloy.

Each of a connection end face of the first wire to the second wire and a connection end face of the second wire to the first wire may be nearly perpendicular to the axial direction of both the wires.

The guide wire may be used in such a manner that the joining portion between the first wire and the second wire be located in a living body.

As described above, according to the present invention, it is possible to provide a guide wire excellent in operationality.

To be more specific, it is possible to provide a guide wire capable of easily, certainly reshaping a distal end portion and exhibiting, at its proximal end portion, a high flexibility and a high resistance against reforming into a curved shape, thereby enhancing the operationality of the guide wire.

According to the present invention, it is possible to provide a guide wire including a distal end portion excellent in flexibility and a proximal end portion excellent in rigidity, thereby enhancing the pushability, torque transmission performance, and trackability of the guide wire.

BRIEF DESCRIPTION OF THE DRAWINGS

These and other objects, features, and advantages of the present invention will become more apparent from the following detailed description in conjunction with the accompanying drawings, wherein:

FIG. 1 is a longitudinal sectional view showing a first embodiment of a guide wire of the present invention;

FIG. 8 is a longitudinal sectional view showing a fifth embodiment of a guide wire of the present invention;

FIG. 10 is a longitudinal sectional view showing a sixth embodiment of a guide wire of the present invention;

FIG. 12 is a longitudinal sectional view showing an eighth embodiment of a guide wire of the present invention.

DETAILED DESCRIPTION OF THE PREFERRED EMBODIMENTS

Figure 2A:
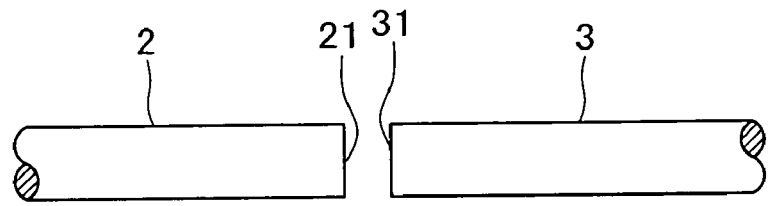
FIGS. 2A to 2D show a procedure for joining a first wire and a second wire of the guide wire shown in FIG. 1 to each other.
Figure 2B:
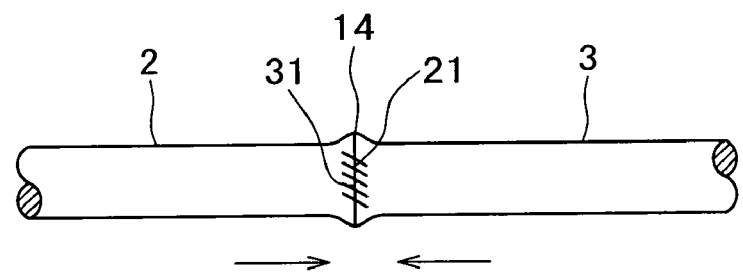
Figure 2C:
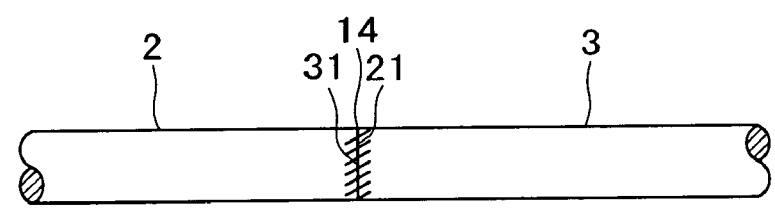
Figure 2D:
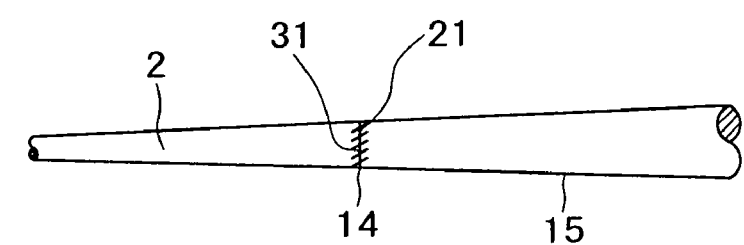

A guide wire of the present invention will now be described in detail by way of preferred embodiments shown in the accompanying drawings.

FIG. 1 is a longitudinal sectional view of a first embodiment of a guide wire of the present invention, and FIGS. 2A to 2D are views showing a procedure for joining a first wire and a second wire of the guide wire shown in FIG. 1 to each other. For convenience of description, the right side in FIG. 1 is taken as the "proximal side" and the left side in FIG. 1 is taken as the "distal side". It is to be noted that in FIG. 1, for easy understanding, the dimension of the guide wire in the thickness direction is exaggeratedly enlarged while the dimension of the guide wire in the length direction is shortened, and therefore, the ratio of the thickness to the length is significantly different from the actual ratio.

A guide wire 1A shown in FIG. 1, which is of a type used to be inserted in a catheter, includes a wire body 10 and a spiral coil 4. The entire length of the guide wire 1A (wire body 10) is not particularly limited but is preferably in a range of about 200 to 5,000 mm. The outer diameter of the guide wire 1A is not particularly limited but is preferably in a range of about 0.2 to. 1.2 mm.

The wire body 10 includes a first wire 2 disposed on the distal side, a second wire 3 disposed on the proximal side from the first wire 2, and a third wire 5 disposed on the proximal side from the second wire 3. The first, second, and third wires 2, 3, and 5 are joined to constitute the wire body 10.

A distal end portion of the wire body 10 has an outer-diameter gradually reducing portion 15 with its outer diameter gradually reduced in the direction toward the distal end, thereby gradually reducing the rigidity (flexural rigidity, torsional rigidity) of the wire body 10 in the direction toward the distal end. As a result, the distal end portion of the guide wire 1A has a high flexibility, to improve the trackability and safety to a blood vessel.

According to this embodiment, the outer-diameter gradually reducing portion 15 is formed in-a region from a distal end portion of the third wire 5 to the distal end of the first wire 2. In this embodiment, the outer-diameter gradually reducing portion 15 is tapered such that the outer diameter is continuously reduced with a nearly constant reduction ratio in the direction toward the distal end. In other words, the taper angle of the outer-diameter gradually reducing portion 15 is kept nearly constant along the longitudinal direction. Unlike such a configuration, the reduction ratio of the outer diameter of the outer-diameter gradually reducing portion 15 (taper angle of the outer-diameter gradually reducing portion 15) may be changed along the longitudinal direction. For example, portions in each of which the reduction ratio of the outer diameter is relatively large and portions in each of which the reduction ratio of the outer diameter is relatively small may be alternately repeated by a plurality of numbers. In this case, the outer-diameter gradually reducing portion 15 may have a portion in which the reduction ratio of the outer diameter in the direction toward the distal end becomes zero.

The first wire 2 is a wire member made from a metal material having elasticity. In particular, the first wire 2 is configured as a reshapable wire. The guide wire 1A having such a first wire 2 at the distal end portion is advantageous in that if the distal end portion (first wire 2) of the guide wire 1A is bent in a desired shape by a hand or fingers of an operator, the first wire 2 is plastically deformed and is kept in the desired shape.

According to the present invention, since the reshapable first wire 2 is provided at the distal end portion of the guide wire 1A, it is possible to simply make the distal end portion of the guide wire 1A reshapable without the need of provision of any additional member such as a reshapable ribbon. This is effective to facilitate production of the guide wire 1A and hence to reduce the production cost of the guide wire 1A.

The material for forming the first wire 2 is not particularly limited insofar as the first wire 2 made from the material is reshapable, but may be selected from metal materials, for example, stainless steels (all kinds specified under SUS, for example, SUS304, SUS303, SUS316, SUS316L, SUS316J1, SUS316J1L, SUS405, SUS430, SUS434, SUS444, SUS429, SUS430F, and SUS302), piano wires, and cobalt alloys. In particular, stainless steels are preferable. The guide wire 1A having, at its distal end portion, the first wire 2 made from a stainless steel is preferable in that the distal end portion of the guide wire 1A is easily reshapable and the reshaped shape of the distal end portion is firmly kept.

The length of the first wire 2 is not particularly limited but is preferably in a range of about 10 to 1,000 mm, more preferably, about 10 to 50 mm or about 100 to 300 mm.

If the length of the first wire 2 is as relatively short as about 10 to 50 mm, the guide wire 1A having such a reshapable first wire 2 at the most distal end portion has the following advantage: namely, the most distal end portion has a reshapable characteristic; and further, in this case, since a distal side portion, excluding the most distal end portion, of the guide wire 1A is formed by the second wire 3 made from a pseudo-elastic alloy as will be described later, the distal side portion (second wire 3) has a high flexibility and thereby has an excellent trackability to a blood vessel complicatedly curved or bent, and is not plastically deforming to thereby prevent degradation of the operationality due to plastically deforming of the first wire 2 during use of the guide wire 1A.

If the length of the first wire 2 is as relatively long as about 100 to 300 mm, the guide wire 1A having such a reshapable first wire 2 at the distal end portion has the following advantage: namely, since nearly the whole of a portion of the guide wire 1A, which is protruded (exposed) from the distal opening of a catheter used together with the guide wire 1A to enter a blood vessel, is formed by the first wire 2 having a relatively high elastic modulus, the portion has a high rigidity (flexural rigidity, torsional rigidity) and improves the pushability and the torque transmission performance for transmitting an operational force on the proximal side to the distal side, thereby enhancing the operationality of the guide wire 1A.

The distal end of the second wire 3 is joined to the proximal end of the first wire 2. The second wire 3 is a wire member having elasticity. The length of the second wire 3 is not particularly limited but is preferably in a range of about 20 to 4,800 mm.

The second wire 3 is made from an alloy having pseudo-elasticity (hereinafter, referred to as "pseudo-elastic alloy"). A portion, formed of the second wire 3 made from such a pseudo-elastic alloy, of the guide wire 1A is relatively flexible, good in restoring performance, and no or less plastically deforming. Accordingly, in the guide wire 1A, the distal end portion formed of the first wire 2 is reshapable, whereas the portion formed of the second wire 3 has excellent trackability to a blood vessel complicatedly curved or bent, and has a resistance against plastically deforming to certainly prevent degradation of the operationality due to plastically deforming during use. As a result, the guide wire 1A exhibits a high operationality.

Pseudo-elastic alloys include those of a type in which the stress-strain curve in a tensile test has any shape, those of a type in which a transformation point such as As, Af, Ms, or Mf can be significantly measured or not measured, and all of a type in which the shape is greatly deformed by stress and then restored nearly to an original shape by removal of stress. A preferable pseudo-elastic alloy is a superelastic alloy, and therefore, it is preferred that the second wire 3 be made from a superelastic alloy.

Examples of pseudo-elastic alloys include Ni—Ti alloys such as a Ni—Ti alloy containing Ni in an amount of 49-52 atomic %. Examples of preferable superelastic alloys include, in addition to the above Ni—Ti alloys, a Cu—Zn alloy containing Zn in an amount of 38.5 to 41.5 wt %, a Cu—Zn—X alloy containing X in an amount of 1 to 10 wt % (X: at least one kind selected from a group consisting of Be, Si, Sn, Al, and Ga), and an Ni—Al alloy containing Al in an amount of 36 to 38 atomic %. Of these materials, the Ni—Ti alloy is preferable.

In the guide wire 1A, the first wire 2 and the second wire 3 are joined (fixed) to each other by welding. A joining portion (welded portion) 14 between the first wire 2 and the second wire 3 has a high joining strength, to certainly transmit a torsional torque or pushing force from the second wire 3 to the first wire 2.

In this embodiment, a connection end face 21 of the first wire 2 to the second wire 3 and a connection end face 31 of the second wire 3 to the first wire 2 are respectively formed to be a plane nearly perpendicular to the axial (longitudinal) direction of both the wires 2 and 3. This significantly facilitates processing for forming the connection end faces 21 and 31, to achieve the above-described effects without complicating the steps for producing the guide wire 1A.

It is to be noted that each of the connection end faces 21 and 31 may be tilted relative to the plane perpendicular to the axial (longitudinal) direction of both the wires 2 and 3, or formed to be a recessed or raised shape.

The method of welding the first wire 2 and the second wire 3 to each other is not particularly limited but is generally exemplified by spot welding using laser or butt resistance welding such as butt seam welding. In particular, to ensure a high joining strength of the welded portion 14, butt resistance welding is preferable.

The procedure of joining the first wire 2 and the second wire 3 to each other by butt seam welding as one example of butt resistance welding will be described with reference to FIGS. 2A to 2D. FIGS. 2A to 2D show steps 1 to 4 of the procedure of joining the first wire 2 and the second wire 3 to each other by butt seam welding.

In the step 1, the first wire 2 and the second wire 3 are fixed (mounted) to a butt welder (not shown).

In the step 2, the connection end face 21 on the proximal side of the first wire 2 and the connection end face 31 on the distal side of the second wire 3 are butted to each other while a specific voltage is applied thereto by the butt welder. With this operation, a fused layer (welded surface) is formed at the contact portion, whereby the first wire 2 and the second wire 3 are strongly joined to each other.

In the step 3, a projection (deformed portion by welding) at the joining portion (welded portion) 14 is removed.

In the step 4, a portion including the joining portion (welded portion 14) is ground to form the outer-diameter gradually reducing portion 15 with its outer diameter gradually reduced in the direction toward the distal end. It is to be noted that the procedure may be jumped from the step 2 to the step 4, with the step 3 omitted.

As shown in FIG. 1, the distal end of the third wire 5 is joined to the proximal end of the second wire 3. The third wire 5 is a wire member having elasticity. The length of the third wire 5 is not particularly limited but is preferably in a range of about 100 to 4500 mm.

The third wire 5 is made from a material having an elastic modulus (Young's modulus or modulus of longitudinal elasticity, modulus of rigidity or modulus of transverse elasticity, or bulk modulus) larger than that of the second wire 3. Accordingly, in the guide wire 1A including such a third wire 5, the portion formed of the second wire 3 has an excellent flexibility (trackability to a blood vessel) and a resistance against plastically deforming, whereas the portion formed of the third wire 5 on the proximal side from the second wire 3 has an appropriate rigidity (flexural rigidity, torsional rigidity). As a result, the guide wire 1A becomes firm and improves the pushability and torque transmission performance, thereby enhancing the operationality at the time of insertion of the guide wire 1A.

The material for forming the third wire 5 is not particularly limited insofar as the material has an elastic modulus larger than that of the second wire 3, but is preferably selected from stainless steels and cobalt alloys. If the third wire 5 is made from a stainless steel or a cobalt alloy, the pushability and torque transmission performance of the guide wire 1A can be further enhanced.

The third wire 5 and the second wire 3 are joined (fixed) to each other by welding. A welded portion 16 between the third wire 5 and the second wire 3 has a high joining strength. This makes it possible to obtain the same effect as that described with respect to the welded portion 14. In addition, the procedure of welding the third wire 5 to the second wire 3 may be performed in the same manner as that used for welding the welded portion 14 between the second wire 3 to the first wire 2.

Unlike the above configuration, the third wire 5 and the second wire 3 may be joined to each other by using another means such as a tubular member provided to fixedly cover the distal end portion of the third wire 5 and the proximal end portion of the second wire 3.

The coil 4 is provided so as to cover the distal side portion of the wire body 10. The coil 4 is a member formed by spirally winding a wire, particularly a fine wire. In the configuration shown in FIG. 1, the wire body 10 is disposed in an approximately axially center portion of the coil 4 in such a manner as to be not in contact with the inner surface of the coil 4. It is to be noted that in the configuration shown in FIG. 1, the coil 4 is loosely disposed in such a manner that a slight gap remains between adjacent spirally wound wire portions in a state that no external force is applied to the coil 4; however, the coil 4 may be tightly disposed in such a manner that no gap remains between the adjacent spirally wound wire portions in a state that no external force is applied to the coil 4.

The coil 4 may preferably be made from a metal material such as a stainless steel, a superelastic alloy, a cobalt alloy, a noble metal such as gold, platinum, or tungsten, or an alloy containing such a noble metal. In particular, the coil 4 is preferably made from a radiopaque material such as a noble metal. If the coil 4 is made from such a radiopaque material, the guide wire 1A can exhibit an X-ray contrast performance. This makes it possible to insert the guide wire 1A in a living body while confirming the position of the distal end portion of the guide wire 1A under fluoroscopy. The distal side and proximal side of the coil 4 may be made from different alloys. For example, the distal side of the coil 4 may be formed of a coil made from a radiopaque material and the proximal side of the coil 4 be formed of a coil made from a relatively radiolucent material such as a stainless material. The entire length of the coil 4 is not particularly limited but may be in a range of about 5 to 500 mm.

The proximal end portion and the distal end portion of the coil 4 are fixed to the wire body 10 by a fixing material 11 and a fixing material 12, respectively, and an intermediate portion (close to the distal end) of the coil 4 is fixed to the wire body 10 by a fixing material 13. Each of the fixing materials 11, 12, and 13 is a solder (brazing material). Alternatively, each of the fixing materials 11, 12, and 13 may be an adhesive, other than a solder. In addition, in place of using the fixing material, the coil 4 may be fixed to the first wire 2 by welding. To prevent damage of the inner wall of a blood vessel, the leading end surface of the fixing material 12 is preferably rounded.

According to this embodiment, since the distal side portion of the wire body 10 is covered with the coil 4, the contact area of the distal side portion with the inner wall of a catheter used together with the guide wire 1A is small, with a result that it is possible to reduce the sliding resistance of the guide wire 1A in the catheter. This is effective to further improve the operationality of the guide wire 1A.

In this embodiment, the welded portion 14 is located on the distal side from the proximal end of the coil 4 and is located on the proximal side from the fixing material 13 positioned between the distal end and the proximal end of the coil 4. The fixing material 13 fixes the coil 4 to the first wire 2. The coil 4 is provided so as to cover the whole of the first wire 2 and the distal end portion of the second wire 3. In this way, the coil 4 covers a relatively longer portion of the wire body 10, to further reduce the sliding resistance of the guide wire 1A.

In this embodiment, the wire having a circular shape in cross-section is used for the coil 4; however, the cross-sectional shape of the wire used for the coil 4 may be another shape such as an elliptic shape or a quadrilateral shape (especially, rectangular shape).

In the guide wire 1A, the outer diameter of both the second wire 3 and the first wire 2 is gradually reduced in the direction toward the distal end. To be more specific, the outer diameter of a portion of the guide wire 1A, which extends across the welded portion 14 from a position on the proximal side from the welded portion 14 to a position on the distal side from the welded portion 14, is gradually reduced in the direction toward the distal end. In other words, a portion of the wire body 10, which extends across the welded portion 14 from a position on the proximal side from the welded portion 14 to a portion on the distal side from the welded portion 14, is formed to be a taper shape with its outer diameter gradually reduced in the direction toward the distal end. The rigidity (flexural rigidity, torsional rigidity) of the portion extending across the welded portion 14 is thus moderately reduced in the direction toward the distal end. As a result, even in the portion extending across the welded portion 14 formed by welding the first wire 2 and the second wire 3 made from different materials and thereby being different in rigidity, the rigidity is moderately (smoothly) changed along the longitudinal direction. As a result, it is possible to improve the kink resistance (resistance against sharp bending) of the welded portion 14 and its neighborhood, and hence to enhance the operationality of the guide wire 1A.

Since the first wire 2 is made from a material having an elastic modulus larger than that of the material for forming the second wire 3, the cross-sectional area of a portion on the proximal side from the first wire 2 may be reduced in such a manner that the rigidity of the proximal side from the welded portion 14 be nearly equal to that of the distal side from the welded portion 14.

According to this embodiment, a portion of the wire body 10, which extends across the welded portion 16 from a position on the proximal side from the welded portion 16 to a position on the distal side from the welded portion 16, is similarly formed to be a taper shape with its outer diameter gradually reduced in the direction toward the distal end. As a result, it is possible to improve the kink resistance (resistance against sharp bending) of the welded portion 16 and its neighborhood, and hence to enhance the operationality of the guide wire 1A.

The whole or part of the outer peripheral surface of the guide wire 1A may be subjected to surface treatment capable of suppressing the friction caused by the contact of the guide wire 1A with the inner wall of a catheter used together with the guide wire 1A. This is effective to suppress the friction of the guide wire 1A against the inner wall of the catheter, and hence to further enhance the operationality of the guide wire 1A in the catheter. As one example of such surface treatment, a coating (not shown) made from a hydrophilic material or a hydrophobic material may be provided on the outer peripheral surface of the guide wire 1A.

Examples of the hydrophilic materials for forming the low-friction coating include a cellulose based polymer, a polyethylene oxide based polymer, a maleic anhydride based polymer (for example, a maleic anhydride copolymer such as methylvinylether-maleic anhydride copolymer), an acrylic amide based polymer (for example, polyacrylic amide or polyglycidyl methacrylate-dimethyl acrylic amide [PGMA-DMAA] block copolymer), water-soluble nylon, polyvinyl alcohol, and polyvinyl pyrolidone. Examples of the hydrophobic materials for forming the low-friction coating include fluorocarbon resins such as polytetrafluoroethylene and silicone resins.

Figure 3:
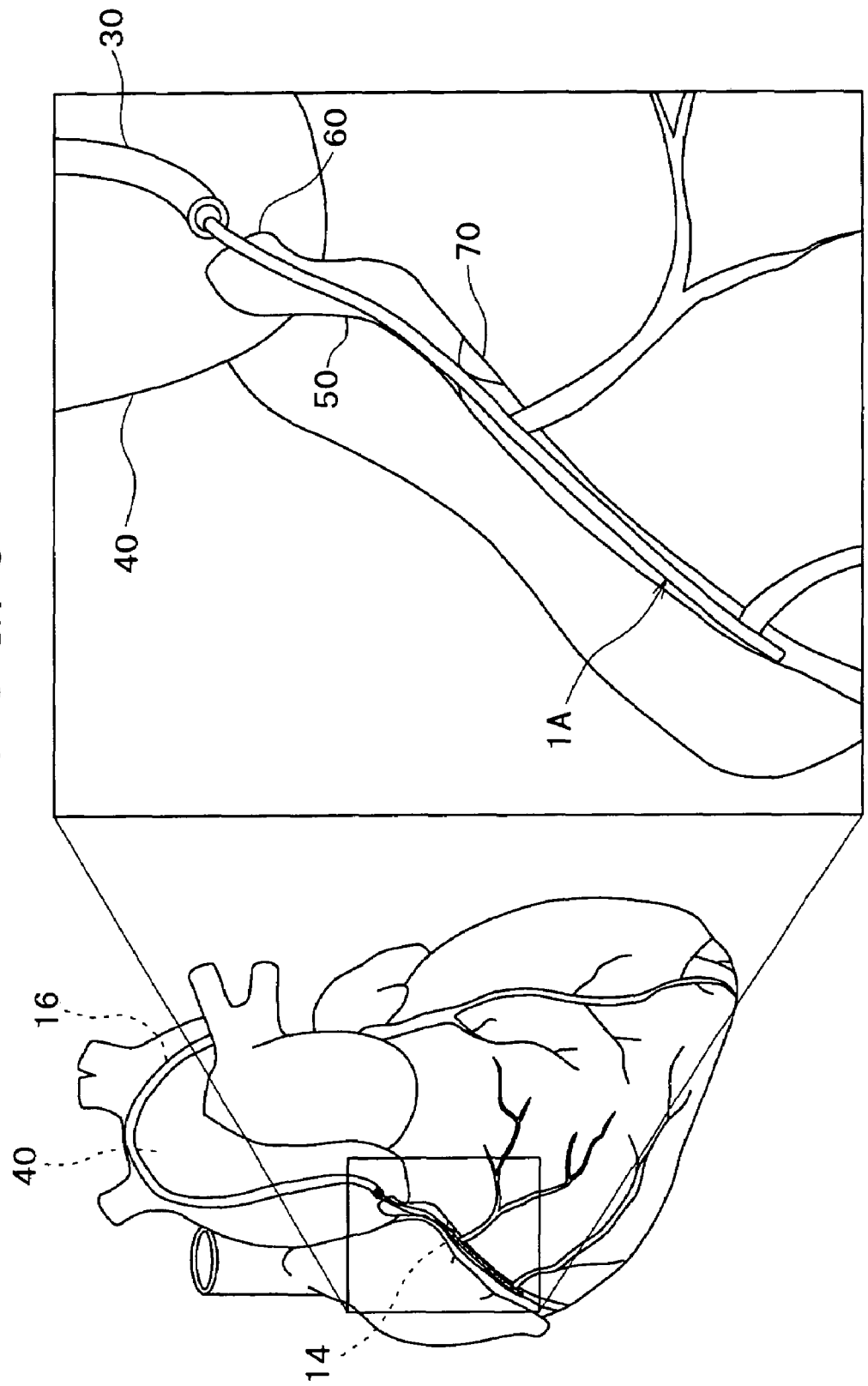
FIG. 3 is a typical view illustrating an example of how to use the guide wire of the present invention.
Figure 4:
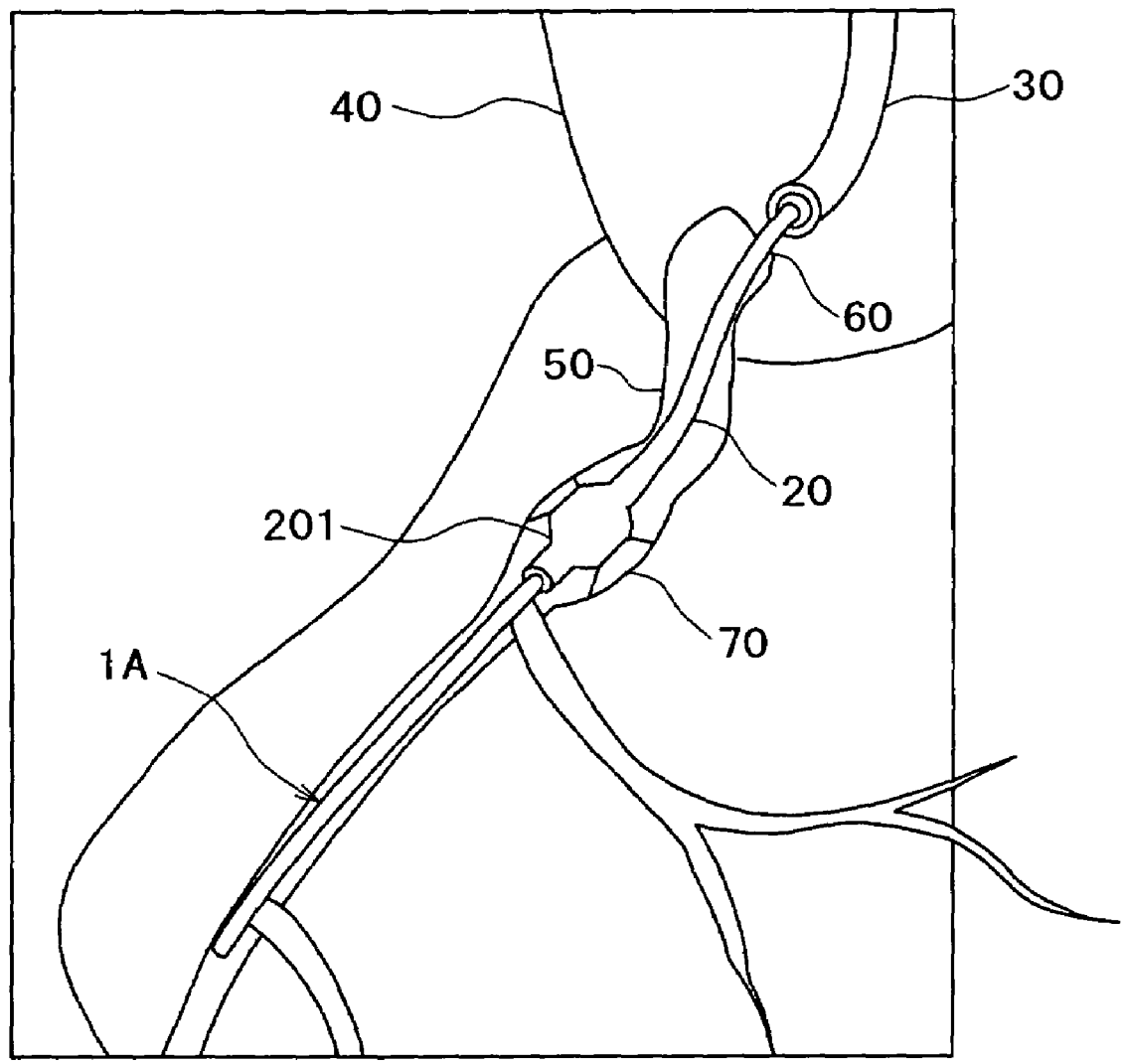
FIG. 4 is a typical view illustrating another example of how to use the guide wire of the present invention.

FIGS. 3 and 4 are views showing the operational state of the guide wire 1A of the present invention during use in the PTCA process.

In FIGS. 3 and 4, reference numeral 40 denotes an aortic arch, 50 is a right coronary artery of a heart, 60 is an ostium of the right coronary artery 50, and 70 is a target angiostenosis portion. Further, reference numeral 30 denotes a guiding catheter for certainly guiding the guide wire 1A from an arteria fermoralis into the right coronary artery 50, and 20 is a balloon catheter having at its distal end an expandable and contractible balloon 201 for dilating the target angiostenosis portion 70.

As shown in FIG. 3, the guide wire 1A is moved in such a manner that the distal end thereof projecting from the distal end of the guiding catheter 30 is inserted in the right coronary artery 50 through the ostium 60 of the right coronary artery 50. The distal end of the guide wire 1A is further advanced in the right coronary artery 50. In this case, the distal end portion of the guide wire 1A has been previously reshaped in a desired shape in order to allow the distal end of the guide wire 1A to selectively insert a branched blood vessel communicated to the target angiostenosis portion 70. The guide wire 1A is stopped when the distal end of the guide wire 1A advances in the branched blood vessel and passes the target angiostenosis portion 70. In this state, an advance path of the balloon catheter 20 is ensured. At this time, the welded portions 14 and 16 of the guide wire 1A are located at positions (in the living body) shown in FIG. 3.

As shown in FIG. 4, the balloon catheter 20 is inserted around the guide wire 1A from the proximal side of the guide wire 1A. The balloon catheter 20 is then advanced in such a manner that the distal end thereof projects from the distal end of the guiding catheter 30, goes ahead along the guide wire 1A, and enters the right coronary artery 50 from the ostium 60 of the right coronary artery 50 (Refer to FIG. 4). The balloon catheter 20 is stopped when the balloon 201 reaches a position corresponding to that of the target angiostenosis portion 70.

A fluid for inflating the balloon 201 is injected in the balloon catheter 20 from the proximal side of the balloon catheter 20 to inflate the balloon 201, thereby dilating the target angiostenosis portion 70 (see FIG. 4). As a result, deposits such as cholesterol adhering on the arterial wall of the target angiostenosis portion 70 are physically compressed against the arterial wall, to eliminate blocking of blood flow.

Figure 5:
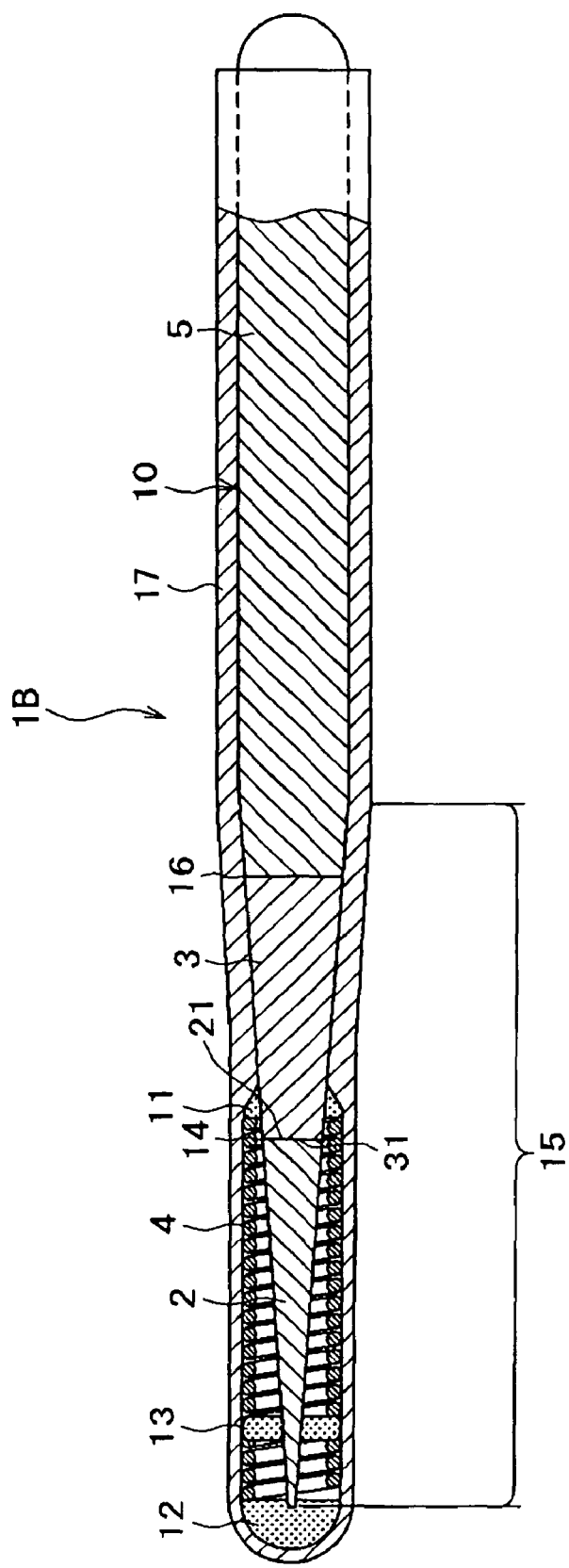
FIG. 5 is a longitudinal sectional view showing a second embodiment of a guide wire of the present invention.

FIG. 5 is a longitudinal sectional view showing a second embodiment of the guide wire of the present invention. The second embodiment of the guide wire of the present invention will be described with reference to FIG. 5, principally, about differences from the first embodiment, with the description of the same features omitted.

A guide wire 1B in this embodiment has the same configuration as that of the guide wire 1A in the first embodiment, except that the outer peripheral surface of the guide wire 1B is covered with a plastic jacket (cover layer) 17 made from a synthetic resin. The plastic jacket 17, for example, being made from polyurethane, is preferably covered with a hydrophilic material.

According to this embodiment, the plastic jacket 17 is provided so as to cover nearly the whole of the outer peripheral surface of the guide wire 1B. In particular, a smooth surface of a welded portion 16 is covered with the plastic jacket 17. Examples of materials for forming the plastic jacket 17 include polyethylene, polyvinyl chloride, polyester, polypropylene, polyamide, polyurethane, polystyrene, polycarbonate, silicone resins, fluorocarbon resins (such as PTFE and ETFE), various kinds of elastomers, and composite materials thereof.

The guide wire 1B including such a plastic jacket 17 is effective to reduce the friction of the guide wire 1B against the inner wall of a catheter used together with the guide wire 1B, and hence to improve the sliding characteristic of the guide wire. This is advantageous in further enhancing the operationality of the guide wire 1B in the catheter.

The plastic jacket 17 is not necessarily provided on the whole of the guide wire 1B, but may be provided, for example, only on a distal side portion (particularly, an outer-diameter gradually reducing portion 15) of the guide wire 1B. The plastic jacket 17 may be provided on a portion, excluding the outer periphery of a coil 4, of the guide wire 1B. In the case where the plastic jacket 17 is provided, there is no need of providing the coil 4 because the sliding characteristic of the guide wire 1B can be sufficiently enhanced only by the plastic jacket 17.

Figure 6:
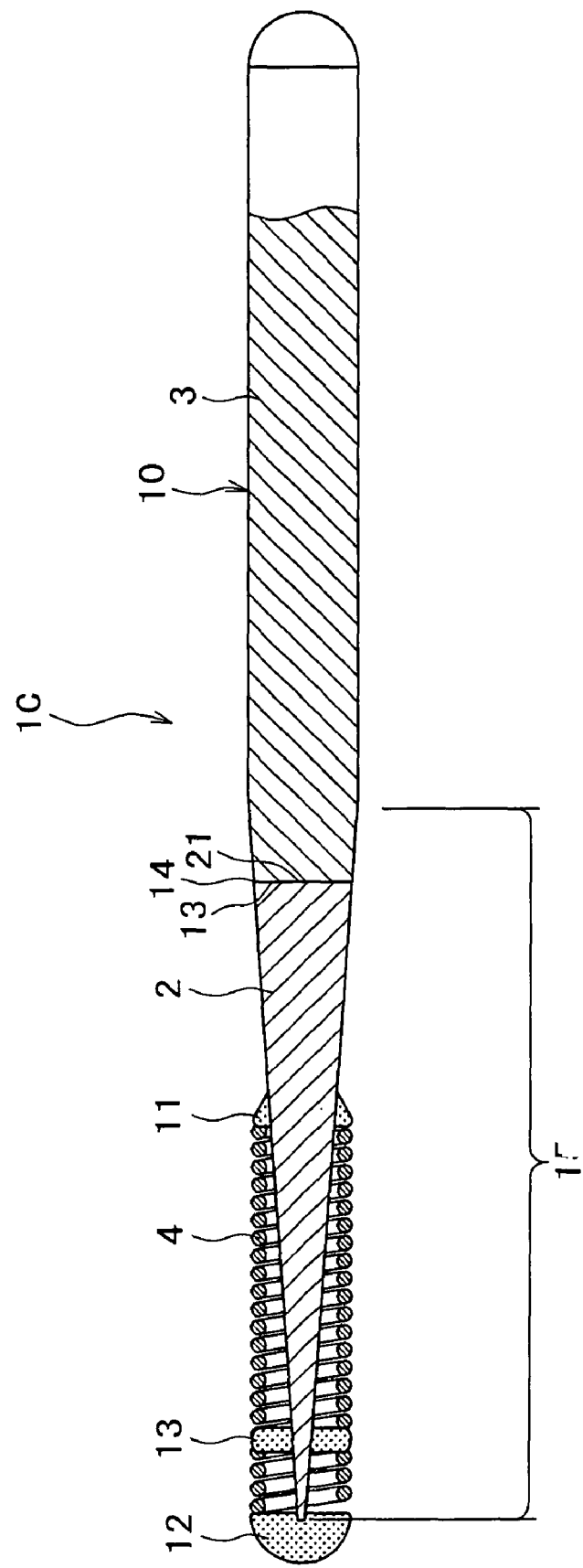
FIG. 6 is a longitudinal sectional view showing a third embodiment of a guide wire of the present invention.

FIG. 6 is a longitudinal sectional view showing a third embodiment of the guide wire of the present invention. The third embodiment of the guide wire of the present invention will be described with reference to FIG. 6, principally, about differences from the first embodiment, with the description of the same features omitted.

A wire body 10 of a guide wire 1C in this embodiment has a first wire 2 and a second wire 3, but does not have the third wire 5. Accordingly, in this embodiment, the whole of a portion on the proximal side from a welded portion 14 is formed of the second wire 3 made from a pseudo-elastic alloy, preferably a superelastic alloy. As a result, such a proximal side portion has a high flexibility and a good resistance against undesirable plastically deforming into a curved shape during use to enhance trackability against a blood vessel complicatedly curved and to prevent degradation of the operationality due to undesirable plastically deforming during use. This is advantageous in enhancing the operationality of the guide wire 1C. In particular, the proximal side portion of the guide wire 1C, which is located outside the body of a patient and is to be operated by a hand of an operator, is no or less plastically deforming to be a curved shape during use, and is therefore easy to be gripped and operated.

According to this embodiment, a welded portion 14 is located on the proximal side from the proximal end of the coil 4. In other words, the whole of the coil 4 including a fixing material 11 (solder) for fixing a proximal end portion of the coil 4 is fixed (joined) to the first wire 2. Accordingly, since any part of the coil 4 is not required to be fixed (joined) to the second wire 3 made from a superelastic alloy such as a Ni—Ti alloy being low in wettability against solder, the fixing (joining) of the coil 4 is facilitated. This makes it possible to easily manufacture the coil 4 and more strongly fix the coil 4.

Like the first embodiment, according to this embodiments the outer diameter of a portion of the wire body 10 (second wire 3 and the first wire 2), which extends across the welded portion 14 from a position on the proximal side from the welded portion 14 to a position on the distal side from the welded portion 14, is gradually reduced in the direction toward the distal end. In other words, the outer diameter of the portion extending across the welded portion 14 is formed to be a tapered shape with its outer diameter gradually reduced in the direction toward the distal end. As a result, even in the portion extending across the welded portion 14, the rigidity of the guide wire 1C is moderately (smoothly) changed along the longitudinal direction, so that it is possible to improve the kink resistance (resistance against sharp bending) of the welded portion 14 and its neighborhood, and hence to enhance the operationality of the guide wire 1C.

The guide wire 1C according to this embodiment may be provided with the same plastic jacket as that described in the second embodiment.

Figure 7:
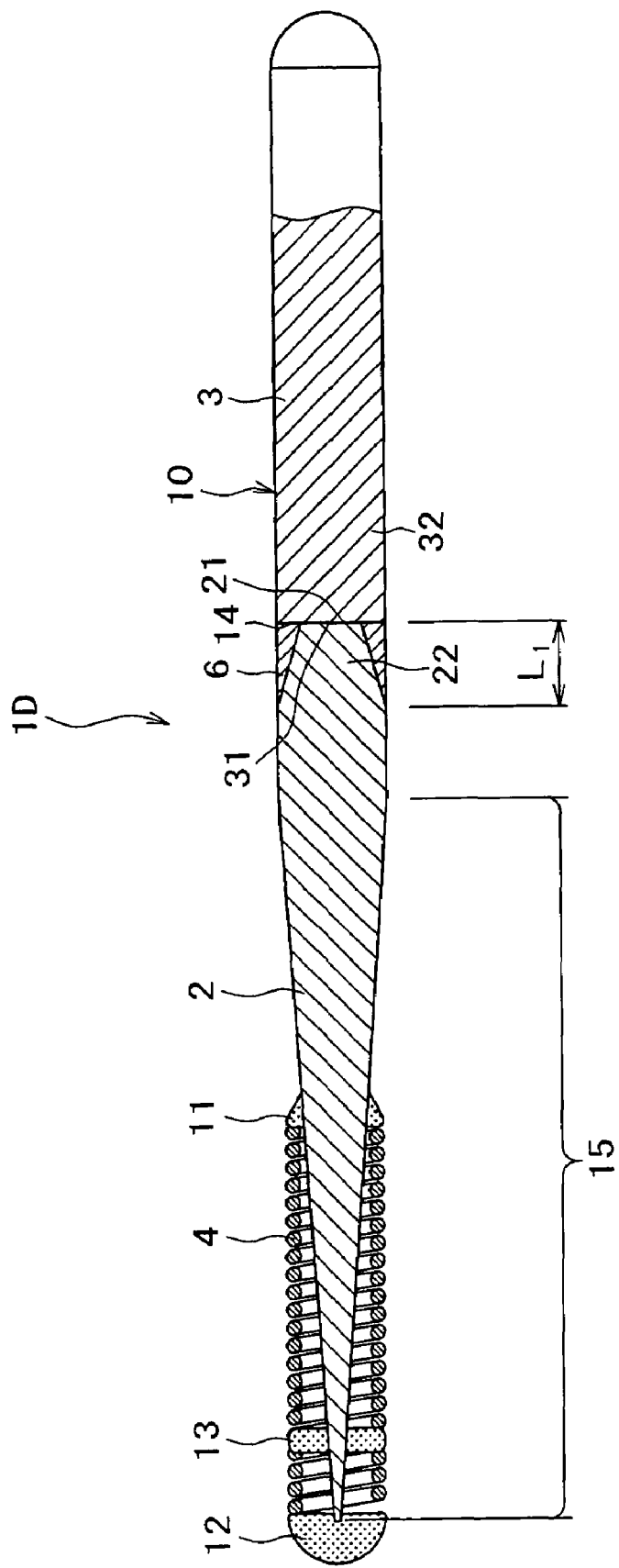
FIG. 7 is a longitudinal sectional view showing a fourth embodiment of a guide wire of the present invention.

FIG. 7 is a longitudinal sectional view showing a fourth embodiment of the guide wire of the present invention. The fourth embodiment of the guide wire of the present invention will be described with reference to FIG. 7, principally, about differences from the third embodiment, with the description of the same features omitted.

A first wire 2 of a guide wire 1D according to this embodiment has, in the vicinity of a welded portion 14, a small cross-sectional area 22 with its cross-sectional area being smaller than that of a distal end portion 32 of a second wire 3. In other words, in a portion from a connection end face 21 to a specific position on the distal side, that is, in the small cross-sectional area portion 22, the cross-sectional area of the first wire 2 is smaller than that of the distal end portion 32 of the second wire 3. In this embodiment, the outer diameter of the small cross-sectional area portion 22 is smaller than that of the distal end portion 32 of the second wire 3, and therefore, the cross-sectional area of the small cross-sectional area portion 22 is smaller than that of the distal end portion 32. In other words, the area of the connection end face 21 is smaller than that of a connection end face 31.

Since the second wire 3 is made from a relatively flexible material, that is, a material having a small elastic modulus such as a superelastic alloy as described above, if the outer diameter of a proximal end portion of the first wire 2 is the same as that of the distal end portion 32 of the second wire 3, the rigidity of the proximal end portion of the first wire 2 becomes larger than that of the distal end portion 32 of the second wire 3. On the contrary, according to this embodiment, the small cross-sectional area portion 22 is provided at the proximal end portion of the first wire 2, and the rigidity (flexural rigidity, torsional rigidity) of the small cross-sectional area portion 22 is made small. As a result, the change in rigidity (flexural rigidity, torsional rigidity) of the welded portion 14 and its neighborhood becomes moderate (smooth) along the longitudinal direction. This makes it possible to improve the kink resistance (resistance against sharp bending) of the welded portion 14 and its neighborhood, and hence to further enhance the operationality of the guide wire 1D.

According to this embodiment, the small cross-sectional area portion 22 includes a portion in which the outer diameter is gradually reduced in the direction toward the proximal end, that is, the cross-sectional area is gradually reduced in the direction toward the proximal end. Accordingly, the rigidity (flexural rigidity, torsional rigidity) of the small cross-sectional area portion 22 is gradually reduced from the distal end to the proximal end thereof in the direction toward the distal end of the guide wire 1D, to thereby make the change in rigidity (flexural rigidity, torsional rigidity) of the guide wire 1D more moderate (smooth) along the longitudinal direction.

In the configuration shown in the figure, the small cross-sectional area portion 22 has, over the entire length, the taper shape with its outer diameter (cross-sectional area) gradually reduced in the direction toward the distal end; however, the small cross-sectional area portion 22 may have a portion having a constant outer diameter (cross-sectional area) on the distal end side. Even in this case, the same effect as that described above can be obtained.

The length of the small cross-sectional area portion 22 (denoted by character $L_1$ in FIG. 7) is not particularly limited but is preferably in a range of about 3 to 50 mm, more preferably, about 3 to 10 mm. If the length $L_1$ is within the above range, the change in rigidity (flexural rigidity, torsional rigidity) of the welded portion 14 and its neighborhood can be made more moderate (smooth) along the longitudinal direction.

In the small cross-sectional area portion 22, the flexural rigidity of the proximal end (connection end face 21) of the first wire 2 is preferably nearly equal to the flexural rigidity of the distal end (connection end face 31) of the second wire 3. With this configuration, the change in rigidity of the welded portion 14 and its neighborhood can be made more moderate (smooth) along the longitudinal direction. In addition, letting the geometrical moment of inertia (determined only by the shape and dimension of the connection end face 21) of the connection end face 21 be $I_1$ and the Young's modulus of the material of the first wire 2 be $E_1$, the flexural rigidity of the material for forming the first wire 2 is expressed by $E_1 \cdot I_1$. On the other hand, letting the geometrical moment of inertia (determined only by the shape and dimension of the connection end face 31) of the connection end face 31 be $I_2$ and the Young's modulus of the material of the second wire 3 be $E_2$, the flexural rigidity of the material for forming the second wire 3 is expressed by $E_2 \cdot I_2$.

The guide wire 1D in this embodiment has a step filling member 6 for filling a stepped portion formed on the outer periphery of the welded portion 14. The stepped portion, which is formed on the outer periphery of the welded portion 14 due to the fact that the outer diameter of the proximal end of the first wire 2 is smaller than that of the distal end of the second wire 3, is filled with the step filling member 6, to thereby prevent the reduction in sliding characteristic of the guide wire 1D due to the presence of the stepped portion.

In the configuration shown in the figure, the step filling member 6 covers the small cross-sectional area portion 22. The outer diameter of the member 6 is kept nearly constant along the longitudinal direction, and the inner diameter of the member 6 is gradually reduced in the direction toward the proximal end. As a result, the outer diameter of a portion, including the welded portion 14 and the small cross-sectional area portion 22, of the guide wire 1D is kept nearly constant along the longitudinal direction. This is effective to more certainly eliminate adverse effect of the stepped portion exerted on the sliding characteristic of the guide wire 1D.

The material for forming the step filling member 6 is not particularly limited, and may be generally selected from resin materials and metal materials. To reduce adverse effect of the member 6 exerted on the rigidity of the guide wire 1D, the member 6 is preferably made from a relatively soft material such as solder, wax, or epoxy resin. The shape of the step filling member 6 is not limited to that shown in the figure but may be any shape such as a coil shape.

In this embodiment, the small cross-sectional area portion 22 is formed into a truncated conical shape; however, the portion 22 may be formed to be a truncated pyramid shape. The formation of the small cross-sectional area portion 22 is not limited to the method of reducing the outer diameter, thereby reducing the cross-sectional area. For example, the small cross-sectional area portion 22 may be formed by providing a cylinder portion having a hollow portion. In this case, the small cross-sectional area portion 22 can be formed without reducing the outer diameter, thus there can be obtained an advantage that a substantial stepped portion is not formed on the outer periphery of the welded portion 14. In other words, it is possible to eliminate the need of provision of the step filling member 6.

Figure 9A:
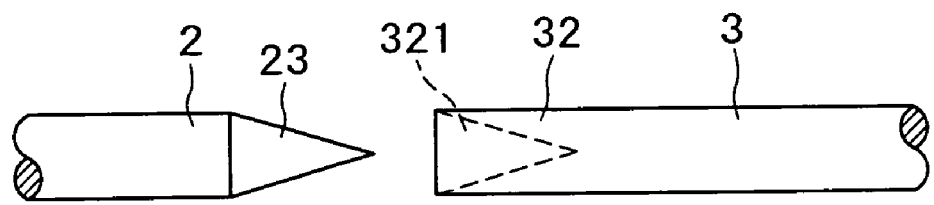
FIGS. 9A to 9C show a procedure for joining a first wire and a second wire of the guide wire shown in FIG. 8.
Figure 9B:
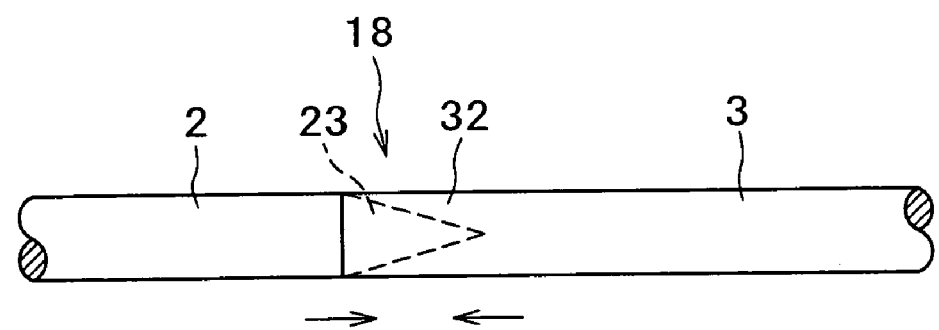
Figure 9C:
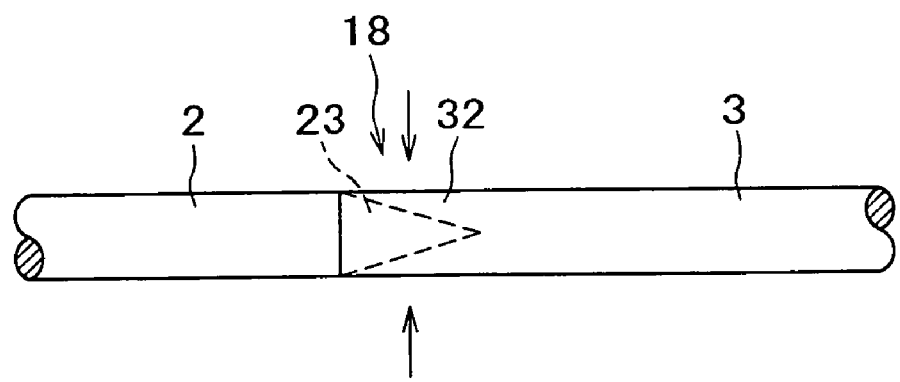

FIG. 8 is a longitudinal sectional view showing a fifth embodiment of the guide wire of the present invention, and FIGS. 9A to 9C are views showing a procedure for joining a first wire and a second wire of the guide wire shown in FIG. 8 to each other. The fifth embodiment of the guide wire of the present invention will be described with reference to these figures, principally, about differences from the third embodiment, with the description of the same features omitted.

A wire body 10 of a guide wire 1E according to this embodiment has an overlapping portion (connecting portion) 18 at which a proximal end portion 23 of a first wire 2 is overlapped to a distal end portion 32 of a second wire 3 in the axial direction of the first and second wires 2 and 3. At the overlapped portion 18, the first wire 2 and the second wire 3 are welded (fixed) to each other. With this configuration, since the area (region) of the welded portion (joining portion) 14 becomes large, it is possible to significantly enhance the joining strength of the welded portion 14.

In this embodiment, the proximal end portion 23 of the first wire 2 is formed to be a conical (or truncated conical) shape with its outer diameter gradually reduced in the direction toward the proximal end, whereas the distal end portion 32 of the second wire 3 has a hollow (recess) portion 321, which is hollow in a state being joined to the first wire 2. The hollow portion 321 is formed to be a conical (or truncated conical) shape with its inner diameter gradually reduced in the direction toward the proximal end. The proximal end portion 23 of the first wire 2 is inserted in the hollow portion 321 of the second wire 3 to form the overlapped portion 18, and then connection end faces of the first and second wires 2 and 3 at the overlapping portion 18 are welded to each other. In this way, according to this embodiment, the welded portion 14 is formed so as to form a conical plane shape.

In the configuration shown in the figure, the outer diameter of the overlapping portion 18 is nearly equal to the outer diameter of a portion, in the vicinity of the distal end of the overlapping portion 18, of the first wire 2, and the outer diameter of a portion, in the vicinity of the proximal end of the overlapping portion 18, of the second wire 3. In other words, the outer diameter of the wire body 10 is kept nearly constant at the overlapping portion 18 and its neighborhood; however, unlike the configuration shown in the figure, the outer diameter of the wire body 10 at the overlapping portion 18 and at its neighborhood may be changed along the longitudinal direction.

As described above, the second wire 3 is made from a relatively soft material, that is, a material having a small elastic modulus such as a superelastic material, and accordingly, if the outer diameter of the second wire 3 is the same as that of the first wire 2, the rigidity (flexural rigidity, torsional rigidity) of the second wire 3 is smaller than that of the first wire 2. At the overlapping portion 18, since the proximal end portion of the first wire 2 is inserted in the distal end portion of the second wire 3, the rigidity (flexural rigidity, torsional rigidity) of the overlapping portion 18 is intermediate between the rigidity (flexural rigidity, torsional rigidity) of the portion, in the vicinity of the distal end of the overlapping portion 18, of the first wire 2 and the rigidity (flexural rigidity, torsional rigidity) of the portion, in the vicinity of the proximal end of the overlapping portion 18, of the second wire 3.

In the guide wire 1E, since the overlapping portion 18 having a medium rigidity is provided between the first wire 2 having a relatively large rigidity and the second wire 3 having a relatively small rigidity, the change in rigidity (flexural rigidity, torsional rigidity) of a portion in the vicinity of the joining portion between the first wire 2 and the second wire 3 becomes moderate (smooth) along the longitudinal direction. As a result, it is possible to improve the kink resistance (resistance against sharp bending) of the portion in the vicinity of the joining portion between the first wire 2 and the second wire 3, and hence to further enhance the operationality of the guide wire 1E.

According to this embodiment, since the proximal end portion 23 of the first wire 2 is overlapped to the distal end portion 32 of the second wire 3 at the overlapping portion 18 as described above, the occupied ratio of the cross-sectional area of the second wire 3 to the total cross-sectional area of the overlapping portion 18 is gradually reduced in the direction toward the distal end. In other words, the occupied ratio of the cross-sectional area of the first wire 2 to the total cross-sectional area of the overlapping portion 18 is gradually increased in the direction toward the distal end. Accordingly, the rigidity of the overlapping portion 18 is nearly equal to that of the second wire 3 at the proximal end of the overlapping portion 18, being gradually increased in the direction toward the distal end, and is nearly equal to that of the first wire 2 at the distal end of the overlapping portion 18. As a result, the change in rigidity (flexural rigidity, torsional rigidity) of the guide wire 1E becomes more moderate (smooth) along the longitudinal direction.

In the configuration shown in the figure, the region in which the occupied ratio of the cross-sectional area of the second wire 3 to the total cross-sectional area of the overlapping portion 18 is gradually reduced in the direction toward the distal end is extended over the entire length of the overlapping portion 18; however, such a region may be provided in part of the overlapping portion 18. Even in this case, the close effect as that described above can be obtained.

According to this embodiment, since the overlapping portion 18 is configured as described above, the flexural rigidity of the overlapping portion 18 is kept constant (that is, isotropic) irrespective of the bending direction. As a result, it is possible to obtain an excellent (natural) operationality of the guide wire 1E.

The length of the overlapping portion 18 (denoted by character $L_2$ in FIG. 8) is not particularly limited but is preferably in a range of about 3 to 100 mm, more preferably, about 5 to 10 mm. If the length $L_2$ is within the above range, the change in rigidity (flexural rigidity, torsional rigidity) of the guide wire 1E can be made more moderate (smooth) along the longitudinal direction.

The overlapping portion 18 may be formed to be a shape having a semi-spherical portion.

The procedure for joining the first wire 2 and the second wire 3 of the guide wire 1E to each other by butt seam welding as one example of butt resistance welding will be described with reference to FIGS. 9A to 9C. FIGS. 9A to 9C show steps 1, 2 and 2' of the procedure of joining the first wire 2 and the second wire 3 to each other by butt seam welding.

In the step 1, the first wire 2 and the second wire 3 are fixed (mounted) to a butt welder (not shown). The proximal end portion 23 of the first wire 2 is previously formed to be a conical shape, and the distal end portion 32 of the second wire 3 is previously formed to be a shape having the conical hollow portion 321.

In the step 2, after the proximal end portion 23 of the first wire 2 is inserted in the hollow portion 321 of the distal end portion 32 of the second wire 3, the first wire 2 and the second wire 3 are butted to each other in the axial direction while a specific voltage is applied thereto by the butt welder. With this operation, a fused layer (welded surface) is formed at the contact surface (contract portion) between the proximal end portion 23 of the first wire 2 and the distal end portion 32 of the second wire 3, whereby the first wire 2 and the second wire 3 are strongly joined to each other. If a projection is formed on the outer periphery of the joining portion (welded portion) by butt welding, such a projection is removed, for example, by grinding.

In the case of carrying out the step 2, according to this embodiment, since the center axis of the first wire 2 is aligned with that of the second wire 3 only by inserting the proximal end portion 23 of the first wire 2 in the hollow portion 321 of the distal end portion 32 of the second wire 3, it is possible to easily align the first wire 2 with the second wire 3. The proximal end portion 23 and the distal end portion 32 are formed to be the shapes capable of preventing application of forces acting to offset the connection end faces of the proximal end portion 23 and of the distal end portion 32 from each other when pressing forces are applied to the first and second wires 2 and 3 in the axial direction at the overlapping portion 18. Accordingly, it is possible to perform welding while certainly preventing occurrence of the offset (slip) between the connection faces of both the wires 2 and 3 when pressing forces are applied to both the wires 2 and 3 in the axial direction at the overlapping portion 18 upon welding.

As shown in the step 2' with reference to FIG. 9C, in place of pressing both the wires 2 and 3 in the axial direction at the overlapping portion 18 in the step 2, the outer peripheral portion of the overlapping portion 18 may be pressed to the inner peripheral side upon welding. In this way, according to this embodiment, since the pressing forces can be applied to the connection faces of the proximal end portion 23 and the distal end portion 32 by pressing the outer peripheral side of the overlapping portion 18 to the inner peripheral side, the degree of freedom in manufacturing is high, so that the manufacturing procedure can be easily performed. The pressing step 2' may be combined with the pressing step 2.

The proximal end portion 23 of the first wire 2 may be formed to be a pyramid shape (or truncated pyramid shape) such as a triangular, square, pentagonal, or hexagonal pyramid or truncated pyramid shape. The hollow portion 321 of the distal end portion 32 of the second wire 3 may be formed to be the corresponding pyramid shape (or truncated pyramid shape). Unlike the configuration shown in the figure, the distal end portion of the second wire 3 may be formed to be a conical or truncated conical shape with its outer diameter gradually reduced in the direction toward the distal end, and the proximal end portion of the first wire 2 be formed to be a shape having a conical or truncated conical shape with its inner diameter gradually reduced in the direction toward the distal end, wherein the distal end portion of the second wire 3 be inserted in the hollow portion of the proximal end portion of the first wire 2.

The configuration of the overlapping portion 18 is not limited to that shown in the figure. For example, each of the proximal end portion 23 of the first wire 2 and the distal end portion 32 of the second wire 3 may be formed into a semi-cylindrical shape, wherein the proximal end portion 23 of the first wire 2 and the distal end portion 32 of the second wire 3 be overlapped to each other to form the overlapping portion 18.

FIG. 10 is a longitudinal sectional view showing a sixth embodiment of the guide wire of the present invention. The sixth embodiment of the guide wire of the present invention will be described with reference to this figure, principally, about differences from the third embodiment, with the description of the same features omitted.

A guide wire 1F according to this embodiment has, at a portion in the vicinity of the proximal side of a welded portion 14, a rigidity imparting member 7 provided so as to cover the outer periphery of a distal end portion 32 of a second wire 3. The provision of the rigidity imparting member 7 is effective to enhance the flexural rigidity of a portion, in the vicinity of the distal end portion 32 of the second wire 3, of the guide wire 1F.

Since the second wire 3 is made from a relatively soft material such as a material having a relatively small elastic modulus, for example, a superelastic alloy as described above, the flexural rigidity of a proximal end portion 23 of the first wire 2 is larger than that of the distal end portion 32 of the second wire 3. As a result, if it is assumed that the rigidity imparting member 7 is not provided, the flexural rigidity of the guide wire 1F is changed between both sides of the welded portion 14. According to this embodiment, however, since the flexural rigidity of the portion in the vicinity of the distal end portion 32 of the second wire 3 is increased by the rigidity imparting member 7, a difference in flexural rigidity between the portion in the vicinity of the distal end portion 32 of the second wire 3 and the proximal end portion 23 of the first wire 2 is small. Accordingly, the change in flexural rigidity of the welded portion 14 and its neighborhood of the guide wire 1F becomes moderate (smooth) along the longitudinal direction. As a result, it is possible to improve the kink resistance (resistance against sharp bending) of the welded portion 14 and its neighborhood of the guide wire 1F, and hence to enhance the operationality of the guide wire 1F. The effect obtained by providing the rigidity imparting member 7 is the same as that for the torsional rigidity of the guide wire 1F.

In this embodiment, the rigidity imparting member 7 is configured as a tubular (cylindrical) member. The outer diameter of the rigidity imparting member 7 is nearly equal to that of the proximal end portion 23 of the first wire 2. In other words, the outer diameter of the distal end portion 32 of the second wire 3 is smaller than that of the proximal end portion 23 of the first wire 2. The distal end face of the rigidity imparting member 7 abuts on a connection end face (proximal face) 21 of the first wire 2. With this configuration, flexural and torsion forces are certainly transmitted from the first wire 2 to the rigidity imparting member 7. This makes it possible to make the change in rigidity (flexural rigidity, torsional rigidity) of the welded portion 14 and its neighborhood more moderate (smooth) along the longitudinal direction.

In the guide wire 1F, each of a boundary portion between the distal end of the rigidity imparting member 7 and the first wire 2 and a boundary portion between the proximal end of the rigidity imparting member 7 and the second wire 3 forms a smooth, continuous plane without a substantial stepped portion. As a result, it is possible to reduce the sliding resistance and hence to enhance the sliding characteristic of the guide wire 1F.

According to this embodiment, each of the outer diameter and the inner diameter of the rigidity imparting member 7 is kept nearly constant along the longitudinal direction (axial direction). Accordingly, the flexural rigidity of the rigidity imparting member 7 is kept constant along the longitudinal direction (axial direction) of the guide wire 1F; however, the rigidity imparting member 7 may be configured such that the flexural rigidity thereof be changed along the longitudinal direction.

The material for forming the rigidity imparting member 7 is not particularly limited but may be selected from metal materials of, for example, a stainless steel, a cobalt alloy, a solder, a brazing material, and a superelastic alloy, and resin (plastic) materials of, for example, a fluorocarbon resin such as polytetrafluoroethylene, an epoxy resin, and polyimide.

The material for forming the rigidity imparting member 7 preferably has an elastic modulus equal to or larger than that of the material for forming the second wire 3. With this configuration, the rigidity (flexural rigidity, torsional rigidity) of the distal end portion 32 of the second wire 3 becomes large. This makes it possible to make the change in rigidity (flexural rigidity, torsional rigidity) of the guide wire 1F more moderate (smooth) along the longitudinal direction.

The method of fixing the rigidity imparting member 7 is not limited. For example, the rigidity imparting member 7 may be fixed by welding, brazing, bonding using an adhesive, or caulking. The rigidity imparting member 7 may be disposed after the first wire 2 and the second wire 3 are welded to each other. Alternatively, after the rigidity imparting member 7 is disposed on the distal end portion 32 of the second wire 3, the first wire 2 and the second wire 3 may be welded to each other. The rigidity imparting member 7 is not limited to a member separately produced and mounted to the second wire 3. For example, the rigidity imparting member 7 may be formed on the outer periphery of the distal end portion 32 of the second wire 3 by metal spraying.

The length of the rigidity imparting member 7 is not particularly limited but is preferably in a range of about 3 to 100 mm, more preferably, about 5 to 10 mm.

The shape of the rigidity imparting member 7 is not limited to that shown in the figure but may be formed to be, for example, a coil shape.

Figure 11:
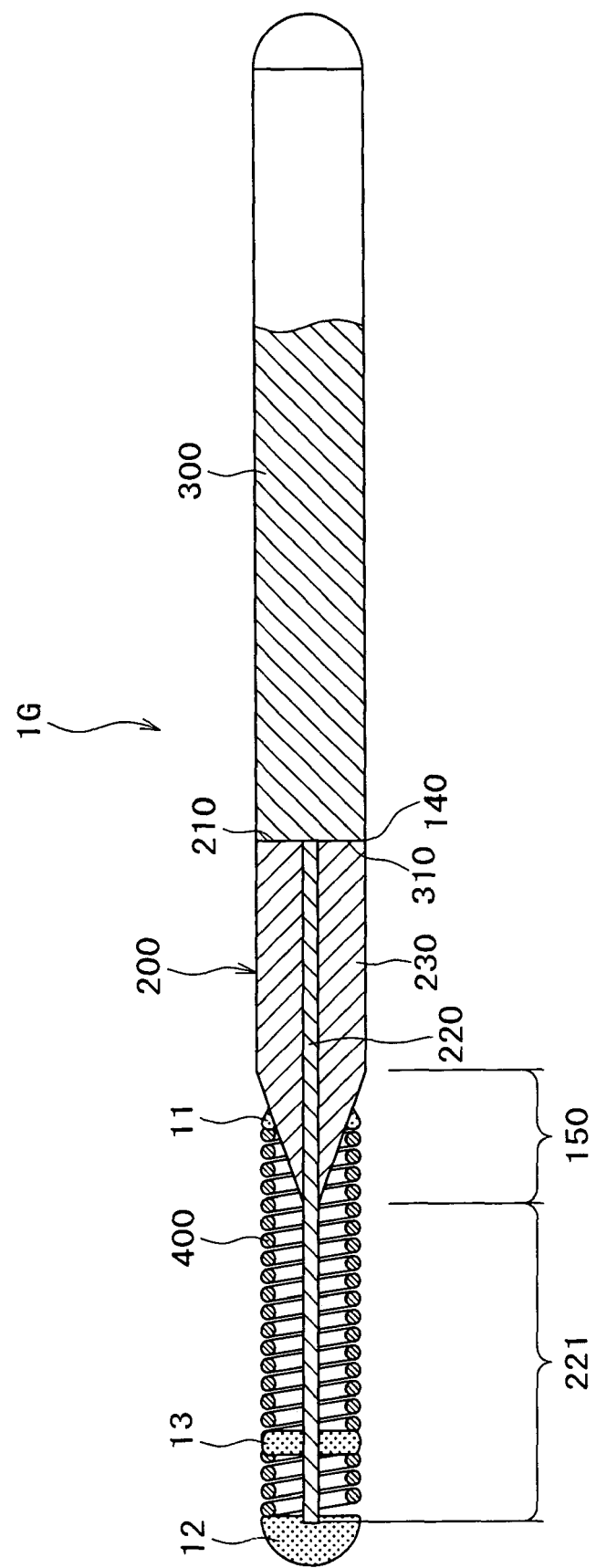
FIG. 11 is a longitudinal sectional view showing a seventh embodiment of a guide wire of the present invention.

FIG. 11 is a longitudinal sectional view showing a seventh embodiment of the guide wire of the present invention. A guide wire 1G shown in FIG. 11, which is of a type used to be inserted in a catheter, includes a first wire 200 disposed on the distal side, a second wire 300 disposed on the proximal side from the first wire 200, and a spiral coil 400. The entire length of the guide wire 1G is not particularly limited but is preferably in a range of about 200 to 5,000 mm.

The second wire 300 is a wire member having elasticity. The length of the second wire 300 is not particularly limited but is preferably in a range of about 200 to 4,800 mm.

The second wire 300 is made from a material having a relatively large elastic modulus (Young's modulus or modulus of longitudinal elasticity, modulus of rigidity or modulus of transverse elasticity, or bulk modulus), and therefore, the second wire 300 has an appropriate rigidity (flexural rigidity, torsional rigidity). As a result, the guide wire 1G becomes firm and improves the pushability and torque transmission performance, thereby enhancing the operationality at the time of insertion of the guide wire 1G. In addition, the material for forming the second wire 300 may have an elastic modulus larger than that of the material for forming a tubular wire 230 (to be described later) of the first wire 200.

The material for forming the second wire 300 is not particularly limited but may be selected from metal materials of, for example, stainless steels (all kinds specified under SUS, for example, stainless steels such as SUS304, SUS303, SUS316, SUS316L, SUS316J1, SUS316J1L, SUS405, SUS430, SUS434, SUS444, SUS429, SUS430F, and SUS302), piano wires, cobalt alloys, and pseudo-elastic alloys (including superelastic alloys). Of these materials, stainless steels are preferable. The use of the second wire 300 made from a stainless steel is effective to enhance the pushability and torque transmission performance of the guide wire 1G.

The proximal end of the first wire 200 is joined (connected) to the distal end of the second wire 300. The first wire 200 is a wire member having elasticity. The length of the first wire 200 is not particularly limited but is preferably in a range of about 10 to 1,000 mm.

The first wire 200 has a tubular wire 230 having elasticity and a core member 220 provided so as to pass through the tubular wire 230. The tubular wire 230 is preferably formed so as to be in close-contact with the core member 220. The core member 220 is a fine wire with its outer diameter kept nearly constant. The core member 220 is made from a material having an elastic modulus larger than that of the tubular wire 230, preferably, a material having an elastic modulus being nearly equal to that of the second wire 300, more preferably, the same material as that of the second wire 300. In particular, the core member 220 is preferably made from a stainless steel.

In other words, the first wire 200 is formed by covering the fine core member 220, which is made from a material having a relatively high elastic modulus equal to or nearly equal to that of the material of the second wire 300, with the tubular wire 230 having an elastic modulus smaller than that of the core member 220.

With this configuration, the rigidity of the first wire 200 can be made sufficiently smaller than that of the second wire 300. As a result, the guide wire 1G has, at its distal portion, a sufficient flexibility against bending, to improve trackability to a blood vessel complicatedly curved or bent, and to thereby enhance the operationality of the guide wire 1G. Even if the first wire 200 is repeatedly deformed, that is, curved or bent, the first wire 200 is no or less plastically deforming to reforming into a curved shape. This prevents degradation of the operationality due to plastically deforming of the first wire 200 during use of the guide wire 1G.

The first wire 200 may be formed by providing an outer layer made from a material different from that of the core member 220, for example, a material having an elastic modulus lower than that of the core member 220 on the surface of the core member 220 in place of the tubular wire 230. Such an outer layer is preferably made from a Ni—Ti alloy, or from a pseudo-elastic material.

Letting the maximum outer diameter of the tubular wire 230 be $R_1$ (mm) and the average outer diameter of the core member 220 be $R_2$ (mm), a ratio $R_2/R_1$ is preferably in a range of about 0.01 to 0.5, more preferably, about 0.02 to 0.3. By setting the ratio $R_2/R_1$ in the above range, it is possible to further enhance the rigidity of the first wire 200, and hence to further improve the operationality of the guide wire 1G.

According to this embodiment, a distal end portion of the first wire 200 is not provided with the tubular wire 230, and is therefore formed of only the core member 220. Such a distal end portion of the first wire 200, from which the core member 220 is exposed, is taken as an exposure portion 221. Accordingly, the exposure portion 221 is made from only a material having a relatively high elastic modulus. Such an exposure portion 221 is reshapable. The term "reshapable" means the property of a wire allowed to be bent into a desired shape and kept in the shape.

To select a branched blood vessel, the distal end portion of the guide wire 1G is often bent into a desired shape by an operator. From this viewpoint, according to this embodiment, since the exposure portion 221 is provided at the distal end portion of the guide wire 1G, the reshaping of the distal end portion of the guide wire 1G can be easily, certainly performed. As a result, it is possible to significantly improve the operationality of the guide wire 1G when the guide wire 1G is inserted in a living body.

The length of the exposure portion 221 (the exposed length of the core member 220 at the distal end portion of the first wire 200) is not particularly limited but is preferably in a range of about 5 to 200 mm, more preferably, about 10 to 150 mm. If the length of the exposure portion 221 is longer than the above range, the operationality of the guide wire 1G may be degraded depending on the material for forming the core member 220. On the other hand, if the length of the exposure portion 221 is shorter than the above range, the reshaping of the distal end portion of the guide wire 1G may become difficult.

According to this embodiment, the tubular wire 230 has an outer-diameter constant portion having a specific length from the proximal end and also has, on the distal side, an outer-diameter gradually reducing portion 150 continuous to the outer-diameter constant portion. The outer-diameter of the outer-diameter gradually reducing portion 150 is gradually reduced in the direction toward the distal end. The provision of the outer-diameter gradually reducing portion 150 is effective to gradually reduce the rigidity (flexural rigidity, torsional rigidity) of the first wire 200 in the direction toward the distal end and hence to improve the flexibility of the distal end portion of the guide wire 1G. This makes it possible to improve trackability to a blood vessel and safety, as well as to prevent sharp bending and the like.

In the configuration shown in the figure, part of the tubular wire 230 is taken as the outer-diameter gradually reducing portion 150; however, the whole of the tubular wire 230 may be taken as the outer-diameter gradually reducing portion 150. A taper angle (reduction ratio of the outer diameter) of the outer-diameter gradually reducing portion 150 may be kept constant or partially changed in the longitudinal direction of the tubular wire 230. For example, portions in each of which the taper angle is relatively large and portions in each of which the taper angle is relatively small are alternatively repeated by a plurality of numbers.

In the tubular wire 230, a portion with its outer diameter kept constant in the longitudinal direction may be formed on part of the outer-diameter gradually reducing portion 150 or on the distal side from the outer-diameter gradually reducing portion 150. For example, a plurality of taper portions in each of which the outer diameter is tapered in the direction toward the distal end may be formed on the tubular wire 230, and a portion with its outer diameter kept constant along the longitudinal direction be formed between adjacent taper portions. Even in this case, the close effect as that described above can be obtained.

Unlike the configuration shown in the figure, the proximal end of the outer-diameter gradually reducing portion 150 may be shifted to the side of the second wire 300. In other words, the outer-diameter gradually reducing portion 150 may be formed across a boundary (joining portion: welded portion 140) between the first wire 200 and the second wire 300.

The material for forming the tubular wire 230 is not particularly limited insofar as the material has an elastic modulus smaller than that of the material for forming the core member 220. For example, the tubular wire 230 may be made from a material selected from metal materials such as a stainless steel. In particular, the tubular wire 230 is preferably made from a Ni—Ti alloy, more preferably, a Ni—Ti alloy having pseudo-elasticity, most preferably, a Ni—Ti alloy having super-elasticity.

Superelastic alloys are relatively flexible, good in restoring performance, and no or less plastically deforming into a curved shape. Accordingly, if the tubular wire 230 is made from a superelastic alloy, the guide wire 1G including such a tubular wire 230 has, at its distal portion (first wire 200), a high flexibility and a good restoring performance against bending, and a high trackability to a blood vessel complicatedly curved or bent, to thereby enhance the operationality of the guide wire 1G. Even if the first wire 200 is repeatedly deformed, that is, curved or bent, the first wire 200 is no or less plastically deforming because of its good restoring performance. This prevents degradation of the operationality due to plastically deforming of the first wire 200 during use of the guide wire 1G.

Examples of superelastic alloys include Ni—Ti alloys such as an Ni—Ti alloy containing Ni in an amount of 49 to 52 atomic %, a Cu—Zn alloy containing Zn in an amount of 38.5 to 41.5 wt %, a Cu—Zn—X alloy containing X in an amount of 1 to 10 wt % (X: at least one kind selected from a group consisting of Be, Si, Sn, Al, and Ga), and an Ni—Al alloy containing Al in an amount of 36 to 38 atomic %. Of these materials, the Ni—Ti alloy is preferable.

According to the present invention, it is particularly preferable that the tubular wire 230 be made from an Ni—Ti alloy and each of the core member 220 and the second wire 300 be made from a stainless steel. With this configuration, the guide wire 1G has, at its distal end portion, a high flexibility, and has, at its proximal end portion, a sufficient rigidity (flexural rigidity, flexural rigidity). As a result, the guide wire 1G has an excellent pushability and a high torque transmission performance to thereby enhance the operationality. The guide wire 1G also has, on the distal side, a high flexibility and a good restoring performance to improve trackability to a blood vessel.

The guide wire 1G in this embodiment also corresponds to an eighth embodiment of the guide wire of the present invention described later. In particular, the exposure portion 221 of the guide wire 1G is equivalent to a distal side wire made from a reshapable metal material disposed on the distal side. A portion located within the tubular wire 230 of the core member 220 and the tubular wire 230 are equivalent to an intermediate wire disposed on the proximal side from the distal side wire, in which at least outer layer is made from a pseudo-elastic alloy. The second wire 300 is disposed on the proximal side from the intermediate wire and is made from a material having an elastic modulus larger than that of the above-described alloy.

The distal side wire preferably extends in the intermediate wire in the axial direction. More preferably, the distal side wire extends to the proximal end of the intermediate wire and the proximal side wire and the distal side wire are welded to each other. The proximal side wire and the distal side wire are preferably made from the same material.

The coil 400 is a member formed by spirally winding a wire, particularly, fine wire, and is disposed so as to cover at least the exposure portion 221. In this embodiment, the coil 400 is disposed so as to cover the exposure portion 221 and the distal end portion of the tubular wire 230. In the configuration shown in the figure, the distal end portion of the first wire 200 is disposed in a nearly axially central portion of the coil 400. The distal end portion of the first wire 200 is disposed in the coil 400 in such a manner as not to be in contact with the inner surface of the coil 400. The joining portion (welded portion 140) between the first wire 200 and the second wire 300 is located on the proximal side from the proximal end of the coil 400.

It is to be noted that in the configuration shown in the figure, the coil 400 is loosely disposed in such a manner that a slight gap remains between adjacent spirally wound wire portions in a state that no external force is applied to the coil 400; however, the coil 400 may be tightly disposed in such a manner that no gap remains between the adjacent spirally wound wire portions in a state that no external force is applied to the coil 400.

The coil 400 may preferably be made from a metal material such as a stainless steel, a superelastic alloy, a cobalt alloy, a noble metal such as gold, platinum, or tungsten, or an alloy containing such a noble metal. In particular, the coil 400 is preferably made from a radiopaque material such as a noble metal. If the coil 400 is made from such a radiopaque material, the guide wire 1G can exhibit an X-ray contrast performance. This makes it possible to insert the guide wire 1G in a living body while confirming the position of the distal end portion of the guide wire 1G under fluoroscopy. The distal side and proximal side of the coil 400 may be made from different alloys. For example, the distal side of the coil 400 may be formed of a coil made from a radiopaque material and the proximal side of the coil 400 be formed of a coil made from a relatively radiolucent material such as a stainless material. The entire length of the coil 400 is not particularly limited but may be in a range of about 5 to 500 mm.

The proximal end portion and the distal end portion of the coil 400 are fixed to the first wire 200 (tubular wire 230 and the core member 220) by a fixing material 11 and a fixing material 12, respectively, and an intermediate portion (close to the distal end) of the coil 400 is fixed to the first wire 200 (core member 220) by a fixing material 13. Each of the fixing materials 11, 12, and 13 is a solder (brazing material). Alternatively, each of the fixing materials 11, 12, and 13 may be an adhesive. In addition, in place of using the fixing material, the coil 400 may be fixed to the first wire 2 by welding. To prevent damage of the inner wall of a blood vessel, the tip end surface of the fixing material 12 is preferably rounded.

According to this embodiment, since the first wire 200 is partially covered with the coil 400, the contact area of the first wire 200 with the inner wall of a catheter used together with the guide wire 1G is small, with a result that it is possible to reduce the sliding resistance of the guide wire 1G in the catheter. This is effective to further improve the operationality of the guide wire 1G.

In this embodiment, the wire having a circular shape in cross-section is used for the coil 400; however, the cross-sectional shape of the wire used for the coil 4 may be another shape such as an elliptic shape or a quadrilateral shape (especially, rectangular shape).

In the guide wire 1G, the first wire 200 and the second wire 300 are integrally joined to each other by welding. Accordingly, a welded portion (joining portion) 140 between the first wire 200 and the second wire 300 has a high joining strength (welding strength) to certainly prevent breakage and damage of the welded portion 140 and hence to ensure high safety of the guide wire 1G. Also, it is possible to certainly prevent an inconvenience caused by reduction in strength of the welded portion 140, for example, an inconvenience that the sharp bending occurs at the welded portion 140 or a torsional torque or a pushing force is less transmitted from the second wire 300 to the first wire 200.

The outer peripheral portion of the welded portion 140 is preferably made substantially smooth by a method, for example, described in the above-described step 3.

The first wire 200 and the second wire 300 may be joined such that at least the tubular wire 230 of the first wire 200 be welded to the second wire 300. In this case, for example, the core member 220 and the second wire 300 may be integrated with each other and the tubular wire 230 be disposed on the outer periphery of the core member 220, and the proximal end of the tubular wire 230 be welded to the distal end of the second wire 300.

In this embodiment, a connection end face 210 of the first wire 200 to the second wire 300 and a connection end face 310 of the second wire 300 to the first wire 200 are respectively formed to be a plane nearly perpendicular to the axial (longitudinal) direction of the guide wire 1G. This significantly facilitates processing for forming the connection end faces 210 and 310 to achieve the above-described effects without complicating the steps for producing the guide wire 1G.

It is to be noted that each of the connection end faces 210 and 310 may be tilted relative to the plane perpendicular to the axial (longitudinal) direction of both the wires 200 and 300, or formed to be a recessed or raised shape.

The method of welding the first wire 200 and the second wire 300 to each other is not particularly limited but is generally exemplified by spot welding using laser or butt resistance welding such as butt seam welding. In particular, to ensure a high joining strength of the welded portion 140, butt resistance welding is preferable. Concretely, welding may be performed in accordance with the above-described steps 1 to 3.

The first wire 200 (core member 220 and the tubular wire 230) and the second wire 300 are preferably joined to each other by welding; however, the first wire 200 and the second wire 300 may be joined to each other by inserting the first wire 200 and the second wire 300 in a tubular member and filling the tubular member with a brazing material or resin, to fix the first and second wires 200 and 300.

In the guide wire 1G, the whole or part of the outer peripheral surface may be covered with a cover (a plastic jacket, not shown) made of synthetic resin. This is effective to reduce the friction of the guide wire 1G with the inner wall of a catheter used together with the guide wire 1G, and hence to improve the sliding characteristic of the guide wire 1G. This makes it possible to enhance the operationality of the guide wire 1G. Examples of the materials for forming the cover include polyethylene, polyvinyl chloride, polyester, polypropylene, polyamide, polyurethane, polystyrene, polycarbonate, fluorocarbon resins (such as PTFE and ETFE), silicone resins, other various kinds of elastomers, and composite materials thereof. In particular, the material having flexibility equal to or less than that of the material for forming the tubular wire 230 is preferable. The location of the cover is not particularly limited. For example, the cover may be provided so as to cover nearly the whole of the guide wire 1G, or to cover only the outer periphery of the distal end portion (outer peripheral surfaces of the first wire 200 and the coil 400).

The whole or part of the outer peripheral surface of the guide wire 1G may be subjected to surface treatment for suppressing the friction caused by contact of the guide wire 1G with the inner wall of a catheter used together with the guide wire 1G. With this treatment, it is possible to suppress the friction of the guide wire 1G with the inner wall of the catheter, and hence to further enhance the operationality of the guide wire 1G in the catheter. Such a surface treatment may be performed, for example, by providing a cover (not shown) made from a hydrophilic material or hydrophobic material on the outer peripheral surface of the guide wire 1G.

Examples of the hydrophilic materials for forming the cover include a cellulose based polymer, a polyethylene oxide based polymer, a maleic anhydride based polymer (for example, a maleic anhydride copolymer such as methylvinylether-maleic anhydride copolymer), an acrylic amide based polymer (for example, polyacrylic amide or polyglycidyl methacrylate-dimethyl acrylic amide [PGMA-DMAA] block copolymer), water-soluble nylon, polyvinyl alcohol, and polyvinyl pyrolidone. Examples of hydrophobic materials for forming the cover include a fluorocarbon resin such as polytetrafluoroethylene, and a silicone resin.

According to this embodiment, since the distal end portion has a high flexibility and the proximal end portion has a high rigidity, it is possible to enhance the pushability, torque transmission performance, and trackability of the guide wire. Also, since at least the tubular wire of the first wire is joined to the second wire by welding, it is possible to enhance the joining strength (welding strength) of the joining portion (welded portion) and hence to certainly transmit a torsional torque and pushing force from the second wire to the first wire. Further, since the core member is exposed at the distal end portion of the first wire, it is possible to impart the reshaping performance to the exposed portion composed of the core member.

The first wire in the guide wire of this embodiment may omit the exposed portion where the core member is exposed. In other words, the guide wire may be constituted to have the core member covered by the tubular wire to its distal end. In this case, the reshapability at the distal end portion of the guide wire can be assured by setting a specific ratio of the outer diameter of the tubular wire to the outer diameter of the core member in the distal end portion of the first wire.

The first wire in the guide wire of this embodiment may be provided, between the core member and the tubular wire, with a layer for any arbitrary purpose (for example, an intermediate layer capable of improving the contactability between the core member and the tubular wire).

FIG. 12 is a longitudinal sectional view showing an eighth embodiment of the guide wire of the present invention.

A guide wire 1H shown in FIG. 12 includes a distal side wire 230 disposed on the distal side, an intermediate wire 600 disposed on the proximal side from the distal side wire 230, having an inner layer 630 being made from the same metal material as that of the distal wire and an outer layer 620 comprising an alloy composition being able to exhibit pseudo-elasticity, and a proximal side wire 300 disposed on the proximal side from the intermediate wire 600. The distal side wire 230 is made from a reshapable metal material. The intermediate wire 600 is composed of an inner layer 630 made from the same metal material as that of the distal side wire 230 and an outer layer 620 made from a pseudo-elastic alloy. The proximal side wire 300 is made from the same metal material as that of the distal side wire 230. The inner layer 630 of the intermediate wire 600 preferably has a plurality of taper portions each of which is tapered in the direction toward the distal end, and the outer layer 620 of the intermediate wire 600 preferably has a plurality of taper portions each of which is tapered in the direction toward the distal end.

The inner layer 630 of the intermediate wire 600, which is made from the same metal material as that of the distal side wire 230, preferably, substantially extends to the distal side wire 230. The inner layer 630 is preferably made from a material having a rigidity higher than that of the material for forming the outer layer 620 such as a stainless steel or a cobalt alloy.

As shown in FIG. 12, the inner layer 630 has a plurality of outer-diameter constant portions and a plurality of taper portions. A first outer-diameter constant portion 631 is located within a coil 400. A first taper portion 632 extends from the proximal end of the first outer-diameter constant portion 631. A second outer-diameter constant portion 633 extends from the proximal end of the first taper portion 632. A second taper portion 634 extends from the proximal end of the second outer-diameter constant portion 633 to the proximal side wire 300. The first outer-diameter constant portion 631 is thinner than the second outer-diameter constant portion 633. The second outer-diameter constant portion 633 is thinner than the proximal side wire 300.

The outer layer 620 is, as described above, made from a pseudo-elastic alloy, which preferably has an alloy composition being able to exhibit pseudo-elasticity such as an Ni—Ti alloy. It is to be noted that the outer layer 620 is not necessarily made from a pseudo-elastic alloy but may be made from any material insofar as the rigidity of the material is lower than that of the inner layer 630.

The outer layer 620 has a plurality of outer-diameter constant portions and a plurality of taper portions. The distal end of a first outer-diameter constant portion 621 reaches the proximal end of the distal side wire 230. A first taper portion 622 extends from the proximal end of the first outer-diameter constant portion 621 to a second outer-diameter constant portion 623. The first outer-diameter constant portion 621, the first taper portion 622, and the second outer-diameter constant portion 623 are located within the coil 400. A second taper portion 624 extends from the proximal end of the second outer-diameter constant portion 623 to a third outer-diameter constant portion 625. The third outer-diameter constant portion 625 has an outer diameter being substantially the same as that of the proximal side wire 300. That is to say, the outer diameter of the guide wire 1H is smoothly shifted from the third outer-diameter constant portion 625 to the proximal side wire 300. The first outer-diameter constant portion 621 is thinner than the second outer-diameter constant portion 623. The second outer-diameter constant portion 623 is thinner than the third outer-diameter constant portion 625.

In the case of inserting the guide wire 1H in a coronary artery, the portion, positioned at the third outer-diameter constant portion 625 of the outer layer 620, of the guide wire 1H is located in an aortic arch, and therefore, such a portion of the guide wire 1H is desired to have a performance capable of transmitting a torque in a curved state. In this regard, when the outer layer 620 is made from a pseudo-elastic alloy, the above portion of the guide wire 1H is no or less plastically deforming to reforming by natural bending, and since the inner layer 630 having a rigidity higher than that of the outer layer 620 extends in the axial direction, the above portion of the guide wire 1H is excellent in torque transmission performance. At the above portion of the guide wire 1H, the ratio of the cross-sectional area of the inner layer 630 to the total cross-sectional area of both the inner layer 630 and the outer layer 620 is preferably less than about 80%, more preferably, 10% to 50%.

At the portion located at the second taper portion 634 of the inner layer 630, of the guide wire 1H, since the outer diameter of the outer layer 620 is kept nearly constant in the direction toward the distal end whereas the outer diameter of the inner layer 630 is gradually thinned in the direction toward the distal end, the flexibility of the above portion of the guide wire 1H is increased in the direction toward the distal end. At the portion located at second taper portion 634 of the inner layer 630, of the guide wire 1H, the ratio of the cross sectional area of the inner layer 630 to the total cross-sectional area of both the inner layer 630 and the outer layer 620 is gradually reduced in the direction toward the distal end. In other words at the portion, located at the second taper portion 634 of the inner layer 630, of the guide wire 1H, the ratio of the cross-sectional area of the outer layer 620 to the total cross-sectional area of both the inner layer 630 and the outer layer 620 is gradually increased in the direction toward the distal end.

The second taper portion 624 of the outer layer 620 contains the first taper portion 632 of the inner layer 630. The length of the second taper portion 624 is preferably different from that of the first taper portion 632. In the configuration shown in the figure, the length of the second taper portion 624 is larger than that of the first taper portion 632. At least part of the intermediate wire 600 preferably has a portion in which the reduction ratio of the outer diameter of the inner layer 630 in the direction toward the distal end is different from the reduction ratio of the outer diameter of the outer layer 620 in the direction toward the distal end. The reduction ratio of the outer diameter of the inner layer 630 in the direction toward the distal end is preferably smaller than the reduction ratio of the outer diameter of the outer layer 620 in the direction toward the distal end. Examples of such portions include a portion located at the first taper portion 632 of the inner layer 630, of the guide wire 1H and a portion located at the first taper portion 622 of the outer layer 620, of the guide wire 1H. The guide wire 1H preferably has at least two portions in each of which the reduction ratios of the inner layer and the outer layer are different from each other.

The intermediate wire 600 has a portion (for example, located at the second taper portion 634 of the inner layer 630) at which the reduction ratio of the outer diameter of the inner layer 630 in the direction toward the distal end is larger than the reduction ratio of the outer diameter of the outer layer 620 in the direction toward the distal end. At the second taper portion 634, since the outer diameter of the outer layer 620 is substantially uniform and therefore the reduction ratio of the outer diameter is zero, the outer diameter of the inner layer 630 is reduced at a specific ratio.

In the case of inserting the guide wire 1H in a coronary artery, a portion located at the second outer-diameter constant portion 623 of the outer layer 620, of the guide wire 1H is positioned in a region from an ascending aorta to a coronary artery, and therefore, the above portion of the guide wire 1H is desired to have a pushability, a torque transmission performance, and a resistance against plastic deformation even in a complicated curved coronary artery. In this regard, in case the outer layer 620 is made from a pseudo-elastic alloy, the above portion of the guide wire 1H is no or less plastically deforming to be a curved shape by natural bending, and since the inner layer 630 having a rigidity higher than that of the outer layer 620 extends in the axial direction, the above portion of the guide wire 1H is excellent in pushability and torque transmission performance. At the above portion of the guide wire 1H, the ratio of the cross-sectional area of the inner layer 630 to the total cross-sectional area of both the inner layer 630 and the outer layer 620 is preferably about 80% or less, preferably, in a range of 10% to 50%. If the above ratio is more than about 80%, the properties of the inner layer 630, particularly, a plastically deformable property is more clearly emerged, so that the rigidity of the above portion of the guide wire 1H becomes high or the portion 623 becomes reshapable to be a curved shape.

The length of the second outer-diameter constant portion 623 is shorter than that of the coil 400. The length of the outer-diameter constant portion, located within the coil 400, of the outer layer 620 is preferably larger than the distal side wire 230.

The distal end of the first outer-diameter constant portion 621 of the outer layer 620 corresponds to the distal end of the first outer-diameter constant portion 631 of the inner layer 630. However, the distal end of the first outer-diameter constant portion 621 may be different from the distal end of the first outer-diameter constant portion 631. That is to say, the distal end of the first outer-diameter constant portion 631 may extend over the distal end of the first outer-diameter constant portion 621. In this case, a portion, not covered with the outer layer 620, of the first outer-diameter constant portion 631 may be regarded as part of the distal side wire 230. The coil 400 is fixed to the first outer-diameter constant portion 621 by a fixing material 13 such as a solder. A portion where the coil 400 is fixed may not be covered with the outer layer 620. If the inner layer 630 is made from a material that can easily bonded to the fixing material 13, it is possible to forcibly fix the coil 400 to the first outer-diameter constant portion 621 by the fixing material 13. The outer layer 620 may be terminated on the proximal side from the fixing material 13. In this case, it is possible to more forcibly fix the coil 400 to the first outer-diameter constant portion 631 of the inner layer 630 by the fixing material 13.

The outer layer 620 and the inner layer 630 may be formed as follows. For example, a wire made from a metal material for forming the inner layer 630 is mechanically ground to be a desired outer diameter to form the first outer-diameter constant portion 631, the first taper portion 632, the second outer-diameter constant portion 633, and the second taper portion 634. Next, a metal material for forming the outer layer 620 such as an Ni—Ti alloy is deposited on the inner layer 630 by sputtering, and mechanically or chemically formed to be a desired shape, to form the desired outer-diameter constant portions and taper portions. If the outer layer is made from a Ni—Ti alloy, the outer layer can desirably exhibit a property having pseudo-elasticity or a property close thereto by a specific heat-treatment of the outer layer.

The distal side wire 230 extends from the first outer-diameter constant portion 631 of the inner layer 630, which is the distal end portion of the intermediate wire 600. The distal end portion of the distal side wire 230 forms a flat plate portion 230. The distal side wire 230 is made from a reshapable metal material such as a stainless steel or a cobalt alloy. The flat plate portion 232 shown in the figure has a substantially rectangular shape in cross-section; however, such a flat plate portion 232 may be formed to be an elliptic or trapezoidal shape in cross-section.

The proximal side wire 300 is preferably made from the same material for forming the distal side wire 230 and the inner layer 630 such as a stainless steel or a cobalt alloy.

In the above-described embodiments, each of the composing elements of the guide wire may be replaced with a composing element having any other configuration exhibiting the similar effect, and may be provided with any other additional element.

The guide wire of the present invention may be configured by combining arbitrary two or more configurations (features) of the above-described embodiments with each other.

It is to be noted that this application is based on Japanese Patent Application Nos. 2002-233905 and 2002-233906 filed on Aug. 9, 2002, the disclosures thereof are incorporated herein by reference.

While the preferred embodiments of the present invention have been described using specific terms, such description is for illustrative purposes only, and it is to be understood that changes and variations may be made without departing from the spirit or scope of the following claims.

What is claimed is:

1. A guide wire comprising:
a first wire disposed on a distal side of said guide wire, said first wire being made from a reshapable and non-super-elastic metal material, said first wire possessing a proximal tip and a distal end;
said first wire being configured to be plastically deformed to a desired shape and maintained in the desired shape upon being bent in the desired shape by a user, the first wire not being a coil, the first wire possessing an outer diameter; and
a second wire disposed on a proximal side from said first wire, said second wire being made from a pseudo-elastic alloy, said second wire possessing a distal tip, the second wire possessing an outer diameter;
wherein the proximal tip of said first wire and the distal tip of said second wire are coaxial;
wherein the first wire includes a proximal end face and the second wire includes a distal end face, the proximal end face of the first wire and the distal end face of the second wire abutting one another and being welded to one another to form a welded portion; and
each of the outer diameters of said first wire and said second wire is gradually reduced in a direction toward the distal end of the first wire in a region extending from a position on the proximal side from the welded portion to a position on the distal side from said welded portion across said welded portion.

2. A guide wire according to claim 1, further comprising:
a third wire disposed on the proximal side from said second wire, said third wire being made from a material having an elastic modulus larger than an elastic modulus of a material forming said second wire;
wherein said second wire and said third wire are joined to each other by welding.

3. The guide wire according to claim 2, said third wire is made from a stainless steel or a cobalt alloy.

4. A guide wire according to claim 1, wherein said first wire has a small cross-sectional area portion having a cross-sectional area smaller than a cross-sectional area of a distal end portion of said second wire in the vicinity of a welded portion between said first wire and said second wire.

5. A guide wire according to claim 1, further comprising:
an overlapping portion in which a proximal end portion of said first wire and a distal end portion of said second wire are overlapped to each other in the axial direction of said first and second wires;
wherein said first wire and said second wire are welded to each other in said overlapping portion.

6. A guide wire according to claim 1, further comprising:
a rigidity imparting member for increasing a flexural rigidity of the vicinity of a distal end portion of said second wire in the vicinity of the proximal side of a welded portion between said first wire and said second wire covering the outer periphery of said second wire.

7. The guide wire according to claim 1, further comprising:
a third wire disposed on the proximal side from said second wire, said third wire being made from a material having an elastic modulus larger than an elastic modulus of a material forming said second wire.

8. The guide wire according to claim 1, wherein said first wire possesses a length in a range of 10 to 1,000 mm.

9. The guide wire according to claim 8, wherein said length of the first wire is a range of 10 to 50 mm.

10. The guide wire according to claim 8, wherein said length of the first wire is in a range of 100 to 300 mm.

11. The guide wire according to claim 1, wherein said welding is butt resistance welding.

12. The guide wire according to claim 1, wherein said welding is spot welding.

13. The guide wire according to claim 1, wherein the proximal end face of the first wire and the distal end face of the second wire are nearly perpendicular to the axial direction of both the first and second wires.

14. The guide wire according to claim 1, further comprising:
a spiral coil covering at least a distal end portion of the first wire, the spiral coil comprising a proximal end and a distal end, a first fixing material fixing the distal end of the spiral coil to the first wire, a second fixing material fixing the spiral coil to the first wire, the second fixing material being proximally spaced from the first fixing material.

15. The guide wire according to claim 14, wherein the welded portion between said first wire and said second wire is located on the proximal side of a proximal end of the coil.

16. The guide wire according to claim 14, wherein the welded portion between the first wire and the second wire is located on a distal side of a proximal end of the coil.

17. The guide wire according to claim 1, wherein the guide wire possesses a rounded distal-most end, and the first wire made of reshapable and non-superelastic metal material possesses a distal end that is fixed to fixing material possessing a rounded end, the rounded end of the fixing material providing the guide wire with said rounded distal-most end.

18. The guide wire according to claim 17, wherein the outer diameter of the first wire from the proximal end of the first wire to the distal end of the first wire is not greater than the outer diameter of the welded portion.

19. The guide wire according to claim 1, wherein the first wire possesses a distal end portion fixed to a rounded fixing material forming a rounded distal-most end of the guide wire, the outer diameter of the first wire gradually reducing from the proximal end of the first wire to the fixing material.

20. A guide wire comprising:
a first wire disposed on a distal side of said guide wire, said first wire being made from a reshapable and non-superelastic metal material, said first wire possessing a proximal tip;
said first wire being configured to be plastically deformed to a desired shape and maintained in the desired shape upon being bent in the desired shape by a user, the first wire not being a coil;
a spiral coil covering at least a distal end portion of said first wire; a second wire disposed on a proximal side from said first wire, said second wire being made from a pseudo-elastic alloy, said second wire possessing a distal tip;
wherein the proximal tip of said first wire and the distal tip of said second wire are welded to each other at a welded portion;
the welded portion comprising a fused layer formed with said first wire and said second wire;
the welded portion between said first wire and said second wire being located on a distal side of a proximal end of said spiral coil;
the proximal tip of said first wire and the distal tip of said second wire are coaxial; and
the first wire includes a proximal end face and the second wire includes a distal end face, the proximal end face of the first wire and the distal end face of the second wire abutting one another and being welded to one another to form the welded portion,
wherein the welded portion is located on a tapered portion of the guide wire.

21. The guide wire according to claim 20, further comprising a first fixing material fixed to a distal end of the spiral coil and a distal end of the first wire to fix the distal end of the spiral coil to the distal end of the first wire, and a second fixing material fixing a portion of the spiral coil other than the proximal end of the spiral coil to the first wire.

22. The guide wire according to claim 20, wherein the spiral coil covers the welded portion and is spaced outwardly away from the welded portion.

23. The guide wire according to claim 20, wherein at least a portion of the spiral coil is located distally beyond a distal end of the welded portion.

24. The guide wire according to claim 20, wherein the spiral coil possesses an axial extent greater than an axial extent of the welded portion.

25. The guide wire according to claim 20, wherein the spiral coil possesses a distal end portion, a proximal end portion and an intermediate portion, and further comprising a first fixing material that fixes the intermediate portion of the spiral coil to the first wire.

26. The guide wire according to claim 25, and further comprising a second fixing material that fixes the distal end portion of the spiral coil to the first wire.

27. The guide wire according to claim 20, wherein the guide wire possesses a rounded distal-most end, and the first wire made of reshapable and non-superelastic metal material possesses a distal end that is fixed to fixing material possessing a rounded end, the rounded end of the fixing material providing the guide wire with said rounded distal-most end.

28. The guide wire according to claim 27, wherein the outer diameter of the first wire from the proximal end of the first wire to the distal end of the first wire is not greater than the outer diameter of the welded portion.

29. The guide wire according to claim 20, wherein the first wire possesses a distal end portion fixed to a rounded fixing material forming a rounded distal-most end of the guide wire, the outer diameter of the first wire gradually reducing from the proximal end of the first wire to the fixing material.

30. A guide wire comprising:
a first wire disposed on a distal side of said guide wire, said first wire being made from a reshapable metal material, said first wire possessing a proximal tip;
said first wire being configured to be plastically deformed to a desired shape and maintained in the desired shape upon being bent in the desired shape by a user, the first wire not being a coil;
a second wire disposed on a proximal side from said first wire, said second wire being made from a pseudo-elastic alloy, said second wire possessing a distal tip;
wherein the proximal tip of said first wire and the distal tip of said second wire are welded to each other at a welded portion;

said first wire being made from a material having an elastic modulus larger than an elastic modulus of the material forming said second wire;

the proximal tip of said first wire and the distal tip of said second wire are coaxial;

the first wire includes a proximal end face and the second wire includes a distal end face, the proximal end face of the first wire and the distal end face of the second wire abutting one another and being welded to one another to form the welded portion;

a third wire disposed on the proximal side from said second wire, said third wire being made from a material having an elastic modulus larger than the elastic modulus of the material forming said second wire;

wherein said second wire and said third wire are joined to each other; and wherein the welded portion is located on a tapered portion of the guide wire.

31. A guide wire comprising:

a first wire disposed on a distal side of said guide wire, said first wire being made from a reshapable and non-super-elastic metal material, said first wire possessing a proximal tip;

said first wire being configured to be plastically deformed to a desired shape and maintained in the desired shape upon being bent in the desired shape by a user, the first wire not being a coil;

a spiral coil covering at least a distal end portion of the first wire; a second wire disposed on a proximal side from said first wire, said second wire being made from a pseudo-elastic alloy, said second wire possessing a distal tip;

the proximal tip of said first wire and the distal tip of said second wire are coaxial;

the first wire includes a proximal end face and the second wire includes a distal end face, the proximal end face of the first wire and the distal end face of the second wire abut one another and are welded to one another to form a welded portion;

the welded portion between said first wire and said second wire is located on the proximal side of a proximal end of the coil; and wherein the welded portion is located on a tapered portion of the guide wire.

32. The guide wire according to claim 31, wherein the outer diameter of the first wire from the proximal end of the first wire to the distal end of the first wire is not greater than the outer diameter of the welded portion.

33. The guide wire according to claim 32, wherein the first wire possesses a distal end portion fixed to a rounded fixing material forming a rounded distal-most end of the guide wire, the outer diameter of the first wire gradually reducing from the proximal end of the first wire to the fixing material.

* * * * *

UNITED STATES PATENT AND TRADEMARK OFFICE
CERTIFICATE OF CORRECTION

| | | |
|---|---|---|
| PATENT NO. | : 7,722,551 B2 | Page 1 of 1 |
| APPLICATION NO. | : 10/635665 | |
| DATED | : May 25, 2010 | |
| INVENTOR(S) | : Hiraku Murayama et al. | |

It is certified that error appears in the above-identified patent and that said Letters Patent is hereby corrected as shown below:

In column 13, line 51, change "12" to --$I_2$--.

Signed and Sealed this
Fourth Day of January, 2011

David J. Kappos
*Director of the United States Patent and Trademark Office*